US009681615B2

(12) United States Patent
Bangera et al.

(10) Patent No.: US 9,681,615 B2
(45) Date of Patent: Jun. 20, 2017

(54) RAPID BREEDING OF PLANTS

(71) Applicant: Elwha LLC, Bellevue, WA (US)

(72) Inventors: Mahalaxmi Gita Bangera, Renton, WA (US); Philip A. Eckhoff, Kirkland, WA (US); Roderick A. Hyde, Redmond, WA (US); Edward K. Y. Jung, Bellevue, WA (US); Wayne R. Kindsvogel, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 1018 days.

(21) Appl. No.: 13/922,445

(22) Filed: Jun. 20, 2013

(65) Prior Publication Data

US 2014/0373445 A1 Dec. 25, 2014

(51) Int. Cl.
*G01N 33/48* (2006.01)
*A01H 1/02* (2006.01)
*A01H 1/04* (2006.01)
*A01H 1/08* (2006.01)
*A01H 4/00* (2006.01)
*A01H 5/10* (2006.01)
*G06F 19/00* (2011.01)

(52) U.S. Cl.
CPC ............... *A01H 1/02* (2013.01); *A01H 1/04* (2013.01); *A01H 1/08* (2013.01); *A01H 4/00* (2013.01); *A01H 5/10* (2013.01); *G06F 19/70* (2013.01)

(58) Field of Classification Search
CPC ...................................................... A01H 1/02
USPC ........................................................ 702/19
See application file for complete search history.

(56) References Cited

U.S. PATENT DOCUMENTS

| | | | |
|---|---|---|---|
| 7,612,258 B2 | 11/2009 | He et al. | |
| 7,941,969 B2 | 5/2011 | Deppermann et al. | |
| 8,312,672 B2 | 11/2012 | Deppermann et al. | |
| 8,395,023 B2 | 3/2013 | Gilbertson et al. | |
| 8,410,336 B2 | 4/2013 | Lutfiyya | |
| 2004/0016015 A1 | 1/2004 | Nguyen et al. | |
| 2010/0037342 A1 | 2/2010 | Johnson et al. | |
| 2010/0076057 A1 | 3/2010 | Sontheimer et al. | |
| 2010/0293673 A1 | 11/2010 | Bull | |
| 2011/0223638 A1 | 9/2011 | Wiedenheft et al. | |
| 2012/0167242 A1 | 6/2012 | Wiles et al. | |

FOREIGN PATENT DOCUMENTS

| | | |
|---|---|---|
| KR | 2010/0129235 A | 12/2010 |
| WO | WO 00/29602 | 5/2000 |
| WO | WO 03/017753 A2 | 3/2003 |
| WO | WO 2006/108284 A1 | 10/2006 |
| WO | WO 2012/052854 A2 | 4/2012 |

OTHER PUBLICATIONS

Chatot et al.; "An Improved Culture Medium Supports Development of Random-bred 1-cell Mouse Embryos in Vitro"; Journal of Reproduction & Fertility Ltd.; Nov. 21, 1988; pp. 679-688; vol. 86.
Hornick et al.; "Isolated Primate Primordial Follicles Require a Rigid Physical Environment to Survive and Grow In vitro"; Human Reproduction; Mar. 28, 2012; pp. 1801-1810; vol. 27, No. 6; Oxford University Press.
Kimura et al.; "Intracytoplasmic Sperm Injection in the Mouse"; Biology of Reproduction; Nov. 16, 1994; pp. 709-720; vol. 52.
Ozakpinar et al.; "Ovarian Stem Cells: From Basic to Clinical Applications"; World Journal of Stem Cells; May 26, 2015; pp. 757-768; vol. 7, No. 4; Baishideng Publishing Group, Inc.
Park et al.; "Bone Morphogenetic Protein 4 Promotes Mammalian Oogonial Stem Cell Differentiation via Smad 1/5/8 Signaling"; Fertility and Sterility; Nov. 2013; pp. 1468-1477; vol. 100, No. 5; Elsevier Science Inc.
Pellicer et al.; "In vitro Fertilization Plus Preimplantation Genetic Diagnosis in Patients With Recurrent Miscarriage: An Analysis of Chromosome Abnormalities in Human Preimplantation Embryos"; Fertility and Sterility; Jun. 1999; pp. 1033-1039; vol. 71, No. 6; Elsevier Inc.
Woods et al.; "The Next (Re)generation of Ovarian Biology and Fertility in Women: Is Current Science Tomorrow's Practice?"; Fertility Sterility; Jul. 2012; pp. 1-16; vol. 98, No. 1; Elsevier Inc.
Xu et al.; "Cross Species Fertilization and Development Investigated by Cat Sperm Injection into Mouse Oocytes"; Journal of Experimental Zoology; Mar. 25, 2011; pp. 349-357; vol. 315; Wiley-Liss Inc.
PCT International Search Report; International App. No. PCT/US2014/042876; Oct. 27, 2014; pp. 1-3.
Hayashi et al.; "Reconstitution of the Mouse Germ Cell Specification Pathway in Culture by Pluripotent Stem Cells"; Aug. 19, 2011; pp. 1-14; vol. 146; Elsevier, Inc.
Murray et al.; "A Proposal to Use Gamete Cycling in Vitro to Improve Crops and Livestock"; Nature Biotechnology; Oct. 2013; pp. 877-880; vol. 31; No. 10; Nature America, Inc.
PCT International Search Report; International App. No. PCT/US2014/042880; Oct. 8, 2014; pp. 1-5.
Bencini et al.; "Wireless Sensor Networks for On-field Agricultural Management Process, Wireless Sensor Networks: Application—Centric Design", 2010; ISBN: 978-953-307-321-7, InTech, DOI: 10.5772/13001; pp. 1-18; available from: http://www.intechopen.com/books/wireless-sensor-networks-application-centric-design/wireless-sensor-networks-for-on-field-agricultural-management-process.
Dewitte et al., "Use of 2n Gametes in Plant Breeding, Plant Breeding"; Dr. Ibrokhim Abdurakhmonov (Ed.), pp. 59-86 plus one additional unnumbered page; published online Jan. 11, 2012; ISBN: 978-953-307-932-5, InTech, DOI: 10.5772/29827. Available from: http://www.intechopen.com/books/plant-breeding/use-of-2n-gametes-in-plant-breeding.
Dowen et al.; "Widespread dynamic DNA methylation in response to biotic stress"; PNAS Early Edition; published online before print Jun. 25, 2012, doi: 10.1073/pnas.1209329109; pp. 1-9.

(Continued)

*Primary Examiner* — Jerry Lin

(57) ABSTRACT

Various embodiments disclosed herein include systems, methods, compositions, and products by process for Rapid-breeding of plants. In certain embodiments, the systems and/or methods are at least partially automated.

17 Claims, 7 Drawing Sheets

(56) References Cited

OTHER PUBLICATIONS

Gaurav, Vishal; "Flow Cytometry of Cultured Plant Cells for Characterization of Culture Heterogeneity and Cell Sorting Applications"; Open Access Dissertations; Paper 370; bearing a date of May 13, 2011; 170 pages.

Geijsen et al.; "Derivation of embryonic germ cells and male gametes from embryonic stem cells"; Nature; Jan. 8, 2004; pp. 148-154; vol. 427; Nature Publishing Group.

Gramzow et al.; "A hitchhiker's guide to the MADS world of plants"; Genome Biology; published Jun. 28, 2010; pp. 1-11; vol. 11; BioMed Central Ltd.

Hayashi et al.; "Offspring from Oocytes Derived from in Vitro Primordial Germ Cell-like Cells in Mice"; Science; Nov. 16, 2012; pp. 971-975; vol. 338; American Association for the Advancement of Science.

He et al.; "Reprogramming of H3K27me3 is Critical for Acquisition of Pluripotency from Cultured *Arabidopsis* Tissues"; PLoS Genet.; Aug. 2012; 8(8):e1002911. doi: 10.1371/journal.pgen.1002911; Epub Aug. 23, 2012; pp. 1-13.

Hohe et al.; "Day Length and Temperature Strongly Influence Sexual Reproduction and Expression of a Novel MADS-Box Gene in the Moss *Physcomitrella patens*"; Plant Biol.; article first published online Jun. 28, 2008; pp. 595-602; vol. 4; Georg Thieme Verlag Stuttgart—New York.

Kranz et al.; "In Vitro Fertilization with Isolated, Single Gametes Results in Zygotic Embryogenesis and Fertile Maize Plants"; The Plant Cell; Jul. 1993; pp. 739-746; vol. 5; American Society of Plant Physiologists.

Kumpatla et al.; "Genomics-Assisted Plant Breeding in the 21st Century: Technological Advances and Progress"; Plant Breeding, Dr. Ibrokhim Abdurakhmonov (Ed.), ISBN: 978-953-307-932-5, InTech, Available from: http://www.intechopen.com/books/plant-breeding/genomics-assisted-plant-breeding-in-the-21st-centurytechnological-advances-and-progress; published online Jan. 11, 2012; 352 pages (hardcover); one reference page included herewith.

Le Cong et al.; "Multiplex Genome Engineering Using CRISPR/Cas Systems"; Science; Feb. 15, 2013; pp. 819-823; vol. 339; American Association for the Advancement of Science.

Levi et al.; "Field evaluation of cotton near-isogenic lines introgressed with QTLs for productivity and drought related traits"; Mol Breeding; published online Sep. 25, 2008; pp. 179-195; vol. 23; Springer Science-Business Media B.V.

Li et al.; "Sensors for Agriculture and the Food Industry"; The Electrochemical Society Interface; Winter 2010; pp. 41-46; last accessed on May 31, 2013.

Mali et al.; "RNA-Guided Human Genome Engineering via Cas9"; Science; Feb. 15, 2013; pp. 823-826; vol. 339; American Association for the Advancement of Science.

Maluszynski et al.; "Doubled Haploid Production in Crop Plants: A Manual"; pp. 1-3 of book description located at www.amazon.com/Double-Haploid-Production-Crop-Plants/dp/1402015445/8ref=sr; printed Jun. 14, 2013.

Memon et al.; "Induction of Callus Through Anther and Ovule Culture in Upland Cotton (*Gossypium hirsutum* L.)"; World Applied Sciences Journal 8 (Special Issue of Biotechnology & Genetic Engineering); 2010; pp. 76-79; IDOSI Publications.

Nayernia et al.; "In Vitro-Differentiated Embryonic Stem Cells Give Rise to Male Gametes that Can Generate Offspring Mice"; Developmental Cell; Jul. 2006; pp. 125-132; vol. 11; Elsevier Inc.

Olmo, H. P.; "Breeding Tetraploid Grapes"; American Society for Horticultural Science; Presented as part of a symposium "Investigations in Polyploidy of Fruits", Sep. 12, 1951; Received for publication Oct. 12, 1951; pp. 284-290; vol. 59.

Pajares, Gonzalo; "Advances in Sensors Applied to Agriculture and Forestry"; Sensors; published Sep. 15, 2011; pp. 8930-8932; vol. 11.

Resende et al.; "Accelerating the domestication of trees using genomic selection: accuracy of prediction models across ages and environments"; New Phytologist; accepted on Aug. 24, 2011; pp. 617-624; vol. 193; New Phytologist Trust.

Singh et al.; "Production of Viable Gametes without Meiosis in Maize Deficient for an Argonaute Protein"; The Plant Cell; Feb. 2011; pp. 443-458; vol. 23; American Society of Plant Biologists.

Van Der Oost, John; "New Tool for Genome Surgery"; Science; Feb. 15, 2013; pp. 768-770; vol. 339; American Association for the Advancement of Science.

Velasco et al.; "The genome of the domesticated apple (*Malus x domestica* Borkh.)"; Nature Genetics; Oct. 2010; pp. 833-839 with two additional unnumbered pages; vol. 42; No. 10; Nature America, Inc.

Wang et al.; "An integrated breeding technology for accelerating generation advancement and trait introgression in cotton"; Plant Breeding; accepted Feb. 16, 2011; pp. 569-573; vol. 130; Blackwell Verlag GmbH.

Wang et al.; "Insights into a Key Developmental Switch and its Importance for Efficient Plant Breeding"; Plant Physiology; Oct. 2000; pp. 523-530; vol. 124; American Society of Plant Physiologists.

Wang et al.; "Wireless sensors in agriculture and food industry—Recent development and future perspective"; Computers and Electronics in Agriculture; accepted Sep. 21, 2005; pp. 1-14; vol. 50; Elsevier B.V.

Wilson et al.; "Plant gametogenesis conservation and contrasts in development"; Reproduction; 2004; pp. 483-492; vol. 128; Society for Reproduction and Fertility.

Yu et al.; "A High-Density Simple Sequence Repeat and Single Nucleotide Polymorphism Genetic Map of the Tetraploid Cotton Genome"; G3 (Bethesda); Jan. 2012; 2(1):43-58. doi: 10.1534/g3.111.001552. Epub Jan. 1, 2012.

RAPID BREEDING OF PLANTS

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

U.S. patent application Ser. No. 13/922,430, entitled RAPID BREEDING OF PLANTS, naming MAHALAXMI GITA BANGERA, PHILIP A. ECKHOFF, RODERICK A. HYDE, EDWARD K. Y. JUNG, WAYNE R. KINDSVOGEL AND LOWELL L. WOOD, JR. as inventors, filed 20 Jun. 2013, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

Described herein for various embodiments include systems, methods, compositions, and products by process for rapid breeding of plants. In certain embodiments, the systems and/or methods are at least partially automated.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
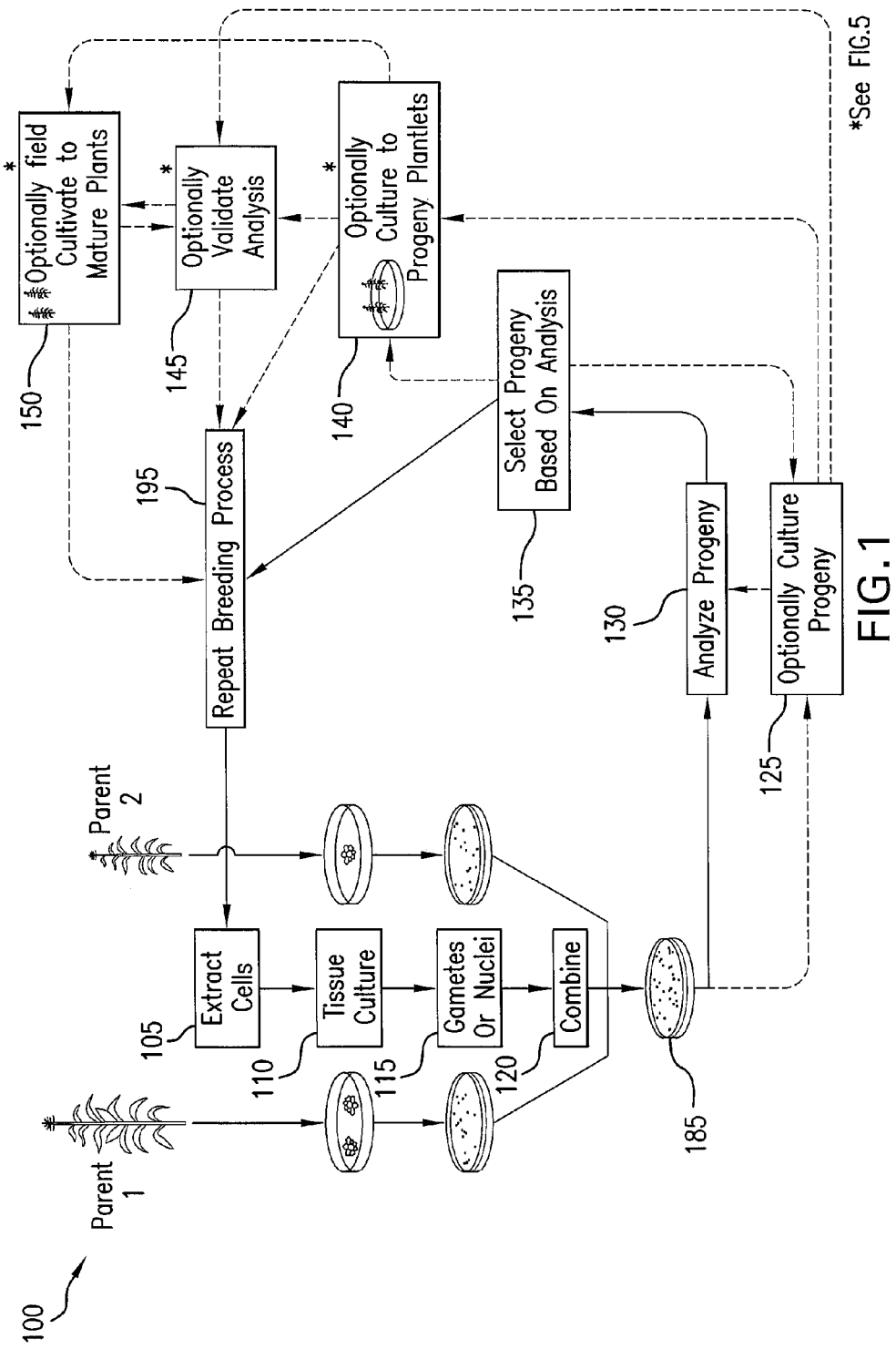
FIG. 1 illustrates a partial view of an embodiment disclosed herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

It is highly beneficial to evolve plant breeding to include characteristics that are desirable without the time-scales usually required for growing plants to maturity for such plants that reproduce sexually. Described herein include various embodiments related to a focused means for selecting and breeding desired cultivars with pre-determined or naturally resulting desired characteristics. Various embodiments disclosed herein provide a higher rate of improvement of desired characteristics, such as increased yield, or drought resistance, among others, which assists in sustainable agriculture practices. In this way, certain embodiments disclosed herein realize multi-generation sequences of gametes by the classic sexual reproductive route, without intervening phenotypes with their attendant complexities and latencies. Furthermore, various embodiments disclosed herein may be utilized to derive new cultivars particularly amenable to certain environmental conditions, or needs for obtaining plant products. Additionally, the disclosed embodiments herein allow for a reduction of labor and field resources for plant breeding, increased capacity to rapidly breed a large number of plants per field unit, as well as an increased capacity to analyze a larger number of plants prior to breeding for desirable characteristics.

Various embodiments disclosed herein relate to genotype-to-genotype generational stepping without an intervening phenotype but instead result from generating male and female gametes directly from plant stem cells. For example, first generation stem cells are induced to derive gametes, which are bred. The resulting fertilized seed includes an embryo from which second generation stem cells may be obtained, if additional breeding is desired. This multi-generational cycling of gametes in vitro (CoGiV) allows for allele valuation and selection for rapid and efficient directed evolution of the particular plant species toward one or more desired characteristics. For example, for specific agricultural crops it is desirable to increase the number of progeny and decrease the amount of time needed to screen and select the particular progeny. In another example, it is desirable to increase the precision of breeding-generated phenotypes or the breadth of accessible genetic variation. As described herein, multiple cycles of breeding and/or selecting are conducted depending on genetic complexity, and desired characteristics.

As disclosed herein, in an embodiment described are an increase in efficiency of Rapid-breeding, and do not require genetic or other modification of the plant genome. However, in an embodiment, modification of plant cells (genetic, epigenetic, transcriptional or translational, etc.) is utilized with the Rapid-breeding process.

At any number of steps, standard breeding techniques may be implemented in conjunction with the steps of the Rapid-breeding methods and systems disclosed herein. For example, in conjunction with the steps of Rapid-breeding of plants, conventional plant crossing may be conducted for selecting starting material (e.g., plant stem cells, gametophytes, or sporophytes, etc.), or once a first, second, third, etc. generation of progeny have been developed. Standard plant crossing includes, for example, obtaining seeds of the first parent plant (may be modified, such as transgenic, or not modified) and a second parent plant and growing the seeds into second generation mature parent plants. Next, pollinating a flower from the first parent with pollen from the second parent and harvesting seeds produced on the parent plant bearing the fertilized flower is conducted. As described herein, introgressing target genes by backcrossing may be accomplished, for example, by first crossing a superior inbred plant (recurrent parent A) to a donor inbred plant (non-recurrent parent B), which carries the suitable gene(s) for the desired characteristic, and the progeny of this cross are selected for the desired characteristic for transference from parent B and selected progeny are mated back to parent A. Following five or more backcross generations with selection for the desired characteristic, the progeny are hemizygous for loci controlling the characteristics being transferred but are similar to the recurrent parent A for almost all other genes. The final backcross generation is self-pollinated to generate progeny which are purebred for the desired gene. However, as described herein, this conventional backcross breeding technique is laborious and time consuming, while the Rapid-breeding methods and systems disclosed herein are able to accomplish the same task in a much more efficient manner. Still, in certain instances one or more backcrosses may be implemented, for example, in conjunction with the Rapid-breeding steps of certain disclosed embodiments.

In an embodiment, a method for plant breeding includes selecting one or more plant stem cells; inducing at least one of the plant stem cells to differentiate into at least one first gamete; combining the at least one first gamete with at least one second gamete of opposite gender for fertilization; and molecularly or microscopically analyzing the progeny resulting from the fertilization.

In an embodiment, the plant stem cell includes a cell isolated from the meristem of a plant (e.g., the apical meristem or lateral meristem). In an embodiment, the plant stem cells are isolated from meristematic tissues such as the root apical meristem, shoot apical meristem, or vascular system ((pro) cambium or vascular meristem, for example). In an embodiment, plant stem cells are isolated from cambium.

As described herein with regard to various embodiments, plant stem cells, similarly to animal stem cells, are totipotent cells that facilitate plant growth and production of plant tissues. Plant stem cells have the ability to self-renew, as well as differentiate into the various different cell types of the plant.

In an embodiment, callus (dedifferentiated cells) is utilized to give rise to totipotent embryogenic cells for utilization with one or more processes described herein. Callus can be initiated from various plant tissues, including but not limited to, immature embryos or parts of embryos, seedling apical meristems, microspores, etc. and result in recipients of genetic information and give rise to fertile plants.

In an embodiment, the cell wall of the plant cell is disrupted or removed (e.g., enzymatically) prior to modification or other use with Rapid-breeding. In an embodiment, meristematic tissue including one or more plant stem cells is utilized for modification as described in the various embodiments disclosed herein.

In an embodiment, a method includes selecting one or more plant stem cells; inducing at least one of the plant stem cells to differentiate into at least one first gamete; combining the at least one first gamete with at least one second gamete of opposite gender for fertilization; and molecularly or microscopically analyzing the embryo resulting from the fertilization.

In an embodiment, microfluidics devices or systems may be utilized for selecting plant stem cells (e.g., by markers) or selecting progeny generated by various embodiments disclosed herein.

In an embodiment, a method includes selecting one or more plant stem cells; inducing at least one of the plant stem cells to differentiate into at least one first gamete of first genetic composition; combining the nucleus of the at least one first gamete with the nucleus of the at least one second gamete of second genetic composition for fertilization; and molecularly or microscopically analyzing the seed resulting from the fertilization. In this particular embodiment, the gametes may be from the same or opposite gender. In an embodiment, the gamete may be from different genetic composition if diversity is desired, or the same genetic composition if the "ideal" or goal genetic composition has already been determined or obtained, or there are particular characteristics desired to be preserved and passed on to the progeny. In an embodiment, the progeny is/are generated by combining the nuclei containing the chromosomes that yield a cell having the ability to sustain itself long enough to be utilized in an additional round of breeding, and/or to go on to develop into a plant. For example, nuclei may be extracted from pollen by purification from the pollen wall by enzymatic, chemical, mechanical, or osmotic means. See, for example, Dewitte, et al., Ch. 4, "Use of 2n Gametes in Plant Breeding," (2012) available online at intechopen dot com, the subject matter of which is incorporated herein by reference. For example, the outer exine layer on the pollen surface is a biopolymer highly resistant to enzymatic or hydrolytic breakdown, as it has evolved to withstand environmental stresses. However, several physical techniques, such as bead beating or chopping of pollen grains, has allowed for release of nuclei from pollen grains sufficient to study the nuclei by flow cytommetry. Id.

In an embodiment, inducing gametes includes inducing plant stem cells first to differentiate to sporophyte stage. In an embodiment, gametes are derived from sporophyte stages without first being induced from stem cells. In an embodiment, inducing gametes includes inducing plant stem cells first to differentiate to gametophye stage. In an embodiment, gametes are derived from gametophyte stage without first being induced from stem cells.

For example, culturing microspores gives rise to pollen, doubled haploid embryos, and apoptotic cells, depending on the culture conditions, including hormones, and sugars. See Wang et al., Plant Physiol. (2000), 124: 523-530, which is incorporated herein by reference. Furthermore, since induction of differentiation is considered a stress condition, specific stress hormones, such as abscisic acid (ABA) and its signal transduction pathway are important factors, as well as lipid transfer proteins, heat shock proteins, and peroxiredoxin anti-oxidant. Id.

In an embodiment, the gametes and/or stem cells are genetically analyzed. Genetic analysis for embodiments described herein includes genetic sequence analysis, ploidy analysis, or marker selection, for example. In an embodiment, mRNA sequence information is obtained at one or more steps in the plant breeding process, for one or more cell types (e.g., stem cells, fertilized seed, gametes, etc.). In an embodiment, marker assisted selection is utilized to screen genetic markers in the very early progeny (zygote, blastocyst, embryo, etc. stage).

In an embodiment, the plant stem cells are treated with one or more transcription factors in order to derive gametes therefrom. For example, MADS-box genes, encoding MADS-domain family of transcription factors that bind DNA, are involved in controlling various cell development and proliferation processes. See Gramzow and Theissen, Genome Biol., 2010, 11:214, which is hereby incorporated by reference. For example, two main types of MADS-domain transcription factors have been characterized, including Type I and Type II, whereas Type I MADS-box genes have usually one or two exons, Type II genes have an average of seven. Id. Likewise, MIKC-type MADS-box genes have been identified as being involved in plant reproductive organ formation, particularly MIKC* and MIKC$^c$. Id. The MADS-box genes are regulated in various ways, including transcriptional regulation by transcription factors (including feedback and feed-forward loops), epigenetic control, and microRNA regulation. Id.

In an embodiment, selecting one or more plant stem cells includes choosing at least one plant stem cell tissue (e.g., meristem tissue) containing plant stem cells based on at least one criteria. In an embodiment, selecting one or more plant stem cells includes choosing from at least one plant stem cell tissue, one or more single cells isolated from the remaining tissue. In an embodiment, one or more single plant cells may be isolated from the plant stem cell tissue, for example, by physical or chemical means (e.g., dissection, flow cytometry, enzymatic extraction, lysis of tissue, etc.).

In an embodiment, inducing at least one of the plant stem cells to differentiate into at least one first gamete includes inducing to differentiate to at least one of a plant ovule, megagametophyte, or egg cell in the case of a female gamete; or at least one pollen grain, microgametophyte, or plant sperm cell in the case of a male gamete.

For example, light intensity, light/dark period, and temperature influence sexual reproduction in plants. See for example, Hohe, et al. (2002), Plant Biol. 4: 595-602, which is incorporated herein by reference. As another example, MADS-box genes are involved in development of sexual reproduction plant components as well as seed development, and root, flower, and fruit development.

In an embodiment, a plant somatic cell is inverse-differentiated into a germ cell precursor and forward-specialized into pre-gametes of either sex and matured in appropriate cellular milieu into fertilization-ready gametes. In an embodiment, plant stem cells are utilized in the process, rather than inverse-differentiated somatic cells. Post-fertilization, in an embodiment the zygote resulting from fertilization is analyzed directly, or cultured to at least a blastula stage, at which stage multiple cells are provided for next-generation pre-gametes. Following maturation into gametes of both sexes, each of these may be employed (in potentially quite wide) crossings aimed at realization of specific allelic traits and/or the exclusion of others, as determined in near-real time by endosperm and/or polar body analysis. As described herein, such Rapid-breeding and analyses may be done at each generation step, and in parallel and/or with highly-automated means that allows for rapid trait selection at each generational step. In an embodiment, the germination viability of the analyzed plant or plant tissue (such as a seed portion or in its entirety) is maintained.

For any given round of breeding, the method includes selecting naturally occurring characteristics that emerge in the crossing of the parent cells. Multiple rounds of such a selection process without the necessity of culturing the resulting offspring yields a rapid-breeding approach that reduces the time needed for natural selection of desirable characteristics to a fraction of that required for traditional plant breeding that allows the offspring to grow up to plantlets or sexually mature adult plants.

For any given round of breeding, one or more genes may be inserted, deleted, or mutated in order to produce a resulting seed bearing the gene or stacks of genes of interest. In an embodiment, for example, the plant stem cells are modified prior to induction of gametes. In another embodiment, the gametes are modified prior to fertilization. In an embodiment, the plant stem cells are modified transgenically by one or more gene insertions, deletions, or mutations. In an embodiment, the plant stem cells are modified epigenetically by altering gene expression through changes in methylation, for example. See for example, Dowen et al., PNAS, pp. 1-9, 2012 available online at pnas.org. For example, in *Arabidopsis*, DNA methylation is deposited at CC, CHG, and CHH sequences (where H is A, C, or T) through three genetically separable pathways to regulate transposon silencing, genomic imprinting, and stable gene silencing. Id. Furthermore, simultaneous disruption of the chromatin remodeling enzymes KYP, SUVH5, and SUVH6 in *Arabidopsis* results in concomitant decrease in cytosine methylation and H3K9me2 levels, and consequently transcriptional reactivation of heterochromatic transposons. Cytosince methylation is established in all sequence contexts by de novo methyltransferases (DRM1/2) through a small RNA-directed DNA methylation (RdDM) pathway. Id. DICER-dependent 21 to 24 nucleotide siRNAs guide Argonaute proteins (AGO4/AGO6) to complementary sequences within the genome, likely through a siRNA: nascent RNA base pairing mechanism, to direct cytosine methylation. Id. Methylation of CGs and CHGs are maintained through DNA replication by MET1, a homologue of the mammalian DNA methyltransferase DNMT1, and the plant-specific CMT3 methyltransferase, respectively. Id. Conversely, active demethylation of methylcytosines is catalyzed by DEMETER (DME) family of DNA glycosylases. Id. Moreover, methylation alterations also assist in immune response to pathogens. Id.

In an embodiment, the one or more modifications of plant cells described herein are reversible. In an embodiment, the one or more modifications occur in DNA of the plant cell nucleus. In an embodiment, the one or more modifications occur in DNA of the mitochondria of the plant cells. In an embodiment, the plant stem cells or gametes are modified by the addition, deletion, or mutation of one or more mRNA molecules or proteins utilized in cell transcription or translation, respectively. In an embodiment, the genetic or epigenetic modification of the plant cells yields transformed progeny plants with a genome that has been altered by the stable integration of a recombinant DNA.

Various embodiments described herein are applicable to a number of plants, including but not limited to grass, fruit, vegetable, flowering trees and plants (e.g., ornamental plants, fruit plants, such as apple and cherry, etc.), grain crops (e.g., corn, soybean, alfalfa, wheat, rye, oats, barley, etc.), other food or fiber crops (e.g., canola, cotton, rice, peanut, coffee, bananas, sugar cane, melon, cucumber, sugar beet, *quinoa*, cassava, potato, onion, tomato, strawberry, *cannabis*, tobacco, etc.), or other plants (including but not limited to banana, bean, broccoli, castorbean, citrus, clover, coconut, Douglas fir, *Eucalyptus*, Loblolly pine, linseed, olive, palm, pea, pepper, poplar, truf, *Arabidopsis thaliana*, *Radiata* pine, rapeseed, sorghum, or Southern pine. Most of the calories consumed by humans come from members of the grass family (e.g., wheat, corn [maize], rice, oats, barley, sorghum, millet, rye, etc.), and grasses make up at least a quarter of all vegetation on Earth, rendering these important food crops worldwide. Various embodiments described herein are applicable to plant cells, seeds, pollen, fruit, zygotes, etc., as disclosed.

Various embodiments disclosed herein are utilized to improve one or more characteristics of a plant by way of rapid selection of desirable naturally occurring characteristics. Various embodiments disclosed herein are utilized to improve one or more characteristics of a modified plant (e.g., genetic, or epigenetic modification) and include rapid selection of desirable characteristics introduced into the plant by modification as described. For example, such characteristics include but are not limited to increased telomere(s), improved agronomic characteristic (e.g., improved yield, nutritional content, physiology, growth or development, stress resistance or tolerance (e.g., disease, pest, or chemical resistance or tolerance), increased seed oil or protein content. In an embodiment, for example, such characteristics include one or more of resistance or tolerance to drought, fungal, bacterial, or viral disease, temperature fluctuation, light fluctuation, exposure to extreme temperature (e.g., heat exposure, or cold exposure), exposure to extreme light conditions (e.g., abundance of light, shade or too little light), insect or worm infestation, low nutrient environment (e.g., low nitrogen or phosphorous availability), osmotic stress, or high plant density. For example, the plant yield includes such properties as plant height, plant structure, assimilation of nutrients (e.g., carbon), pod number or position on the plant, pod shatter, grain size, number of internodes, efficiency of nitrogen fixation, resistance to abiotic or biotic stress, seedling vigor, overall percentage of seed germination, resistance to lodging, growth rate, seed number or size, or seed composition.

In an embodiment, analyzing the resulting progeny (e.g., fertilized seed or resulting plant(let) therefrom) includes analyzing for an improvement in a particular characteristic, whether such characteristic is attributed to a naturally occurring trait or is the result of a modification (e.g., physical, chemical, genetic, epigenetic intervention, etc.). In an embodiment an improvement in a particular characteristic includes an increased level of a particular characteristic in the progeny, relative to a control plant (in certain instances, the control plant may be a parent plant). For example, an increased level of a particular characteristic may be measured as described herein, including increased seed size or increased number of seeds per unit measured.

In an embodiment, analyzing the resulting progeny includes evaluating one or more characteristics including a genetic marker, a single nucleotide polymorphism, a simple sequence repeat, a restriction fragment length polymorphism, a haplotype, a tag single nucleotide polymorphism, a gene, an allele of a genetic marker, a DNA-derived sequence, an RNA-derived sequence, promoter, 5'-untranslated region of a gene, 3'-untranslated region of a gene, microRNA, siRNA, a QTL, satellite marker, transgene, mRNA, high-resolution chromosomal structure and content analyses with microarrays, double stranded mRNA, transcriptional profile, or methylation pattern.

In an embodiment, an improvement in a particular characteristic includes a decreased level of a particular characteristic in the progeny, relative to a control plant (again, in certain instances, the control plant is the parent plant). For example, a decreased level of a particular characteristic may be measured as described herein, including decreased use of water or nutrients from the soil.

The various characteristics described may be analyzed for improvement in several ways. For example, chemistry, cell biology, or molecular biology techniques may be utilized for measuring telomere changes, ploidy, or gene, protein, or mRNA changes, seed biomass, seed content (e.g., oil, carbohydrate, protein, nitrogen, phosphorous, etc. or ratios of one or more of these seed components), epigenetic changes, etc. As another example, ploidy may be evaluated by flow cytommetry or microscopic analysis. In an embodiment, the desired ploidy plants or plant tissues (including seeds) are selected and those that are not of the desired ploidy are removed from the desired ploidy plants/plant tissues. In an embodiment, the plant tissue is analyzed for one or more alleles, or ploidy level of at least one locus.

As another example, an immunoreactive antibody may be utilized to detect the presence or absence of a protein that is expressed or suppressed in the progeny seed or plant tissue.

Other changes, including improvements, in the various characteristics described may be measured by physical means, for example, plant weight, seed weight, seed number per plant, seed number or seed weight per acre, bushels per acre, tons per acre, kilo per hectare, etc. As another example, a small portion of tissue is removed from the fertilized seed without disturbing the viability of the seeds, and such tissue is analyzed by means described herein.

In an embodiment, when autoploid plants (such as alfalfa) are utilized in the described methods, gametes are optionally selected depending on their ploidy, for example, gametes that are bivalents or quadrivalents resulting from meiosis may be selected (univalent or trivalents resulting from triploids are usually sterile). If polyploidy plants are desired for use with various embodiments described herein, inhibition of mitosis artificially induces polyploids. For example, high temperatures or use of chemicals to inhibit mitosis (such as colchicine, EMS, $GA_3$, temperature, trifluralin, $N_2O$, or dinitroanilines) may be used to induce polyploids.

In an embodiment, a polyploidy plant may be desired due to the increased cell size or cell volume (including, for example, enlarged plant organs) that is a result of additional chromosomes. For example, tetraploid grapes yield greater juice content than their diploid counterparts, and ornamental crops with increased numbers of chromosomes have higher quality and size of blossoms. See, for example, Olmo (1952) American. Soc. Hort. Sci. 59: 285-290, which is incorporated herein by reference.

Likewise, in an embodiment doubled haploid cells are desired and may be generated in over 250 plant species. See, for example, Malunszynski, et al., 2003 Doubled haploid production in crop plants. A manual. Kluwer Acad. Pub. Dordrecht, Boston, London, which is incorporated herein by reference. Doubled haploid plants may be produced in vivo or in vitro, for example. Haploid embryos are produced in vivo, for example, by parthenogenesis, pseudogamy, or chromosome elimination following wide crossing.

Doubled haploid plants save time in generating homozygous lines essentially without the need for conventional breeding. In certain embodiments disclosed herein, doubled haploids are utilized for Rapid-breeding. For example, typically the first step for doubled haploid production includes haploidization of the plant with production of haploid seed. Non-homozygous lines are crossed with an inducer parent, resulting in the production of haploid seed, and selection of seed that contains a haploid embryo independent of the ploidy of the endosperm (the process of which normally results in triploid endosperm). Subsequently, selected haploid seeds (that is haploid embryo in the seed) undergo chromosome doubling to generate doubled haploid seeds. Spontaneous chromosome doubling leads to normal gamete production or production of unreduced gametes from haploid cell lineages, while addition of colchicine or other mitotic disruptor can also be used to increase the rate of diploidization. The chimeric plants are self-pollinated to produce diploid (doubled haploid) seed, which is cultivated and/or evaluated and used in hybrid testcross production.

In an embodiment, plant tissue from the doubled haploid is analyzed, and utilized further in methods described herein. Furthermore, by utilizing endosperm tissue derived from a diploid plant, the ploidy level of the particular genetic marker is determined, with a diploid level indicating maternal inheritance and a haploid level indicating paternal inheritance. This is due to the endosperm tissue being triploid, with two copies of the gene derived from the female gamete, which allows for analysis of linkage phase of the parental line by evaluating heterozygous progeny genotypes that indicates different allele frequencies in DNA samples.

For example, maize embryo zygosity includes triploid endosperm and diploid embryo tissue, thus endosperm copy number indicates the zygosity of the embryo, that is, a homozygous endosperm accompanies a homozygous embryo, while a heterozygous endosperm indicates a heterozygous embryo. For example, endosperm that is homozygous for an internal control gene will contain three copies of the gene, whereas the gene of interest varies from 0 to 3, depending on the heritability and zygosity of the resulting progeny.

It is useful to determine zygosity of one or more loci during plant breeding in order to evaluate the degree of fixation, or inbreeding, segregation distortion (i.e., in transgenic germplasm, maternal inheritance testing of for loci that affect gametes).

For example, determination of allelic frequencies assists in determining parental linkages for a specific marker, and comparing allele frequency data between two or more germplasm pools provides guidance with selection of targeted desired characteristics in such a way that as alleles increasing in frequency in conjunction with a shift in distribution of one or more characteristics, such is presumed to be linked to the trait of interest. Furthermore, determining relative allele frequency data assists in construction of genetic linkage maps. For example, several species of plants have had full or partial genomic sequence analysis conducted, including rice varieties, *eucalyptus* varieties, strawberry varieties, apple varieties, grape varieties, tomato varieties, potato varieties, wheat varieties, maize varieties, oil plants, cereal crops, biodiesel crops, various algaes, and others. Thus, genetic sequences for particular plants, or the homologs from other species, are readily available or attainable for use with various embodiments described herein.

In certain embodiments, selected progeny are bulked, depending on the analysis of the resulting genotype. Conversely, if multiple characteristics are analyzed by way of QLT or genomic selection, for example, with varying effects being selected for a particular population, the progeny may keep individual identity preserved, and cultivate the progeny for determination of various combinations of the desired QTL.

In an embodiment, methods disclosed herein relate to introgressing a characteristic into a plant, for example, by removing a sample of cells or nucleic acids from plant tissue (e.g., seeds), and analyzing the nucleic acids extracted from each seed for the presence or absence of at least one genetic marker, selecting seeds from the population based on the results of the nucleic acid analysis, and cultivating a plant for use with a second generation of breeding.

In an embodiment, cycling of gametes in vitro, as described herein, accelerates the introgression of a specific gene or genes into a plant and allow for greater precision by more cycles of recombination.

Likewise, genetic recombination can involve "gene conversion" or the non-reciprocal transfer of DNA from one genotype to another. Utilizing various embodiments disclosed herein, vast populations for rare zygotes with gene conversion at a target locus may be screened to identify a true isogenic derivative rather than a nearly-isogenic backcross derivative in which flanking alleles from the donor may confer undesirable characteristics. Gene conversion may be especially useful for manipulating exotic germplasm in which a desirable gene is often surrounded by undesirable ones and thus methods disclosed herein assist in avoiding intermediate phenotypes.

Sexual plant breeding results in the addition and transfer of chromosomes, which allows for increased diversity in the progeny, and allows for selection of particular desirable characteristics. Chromosome doubling in vitro induces polyploidy, by utilizing mitotic inhibitors such as dinitroaniles and colchicine. As described herein, ploidy status may be determined in a number of cell or molecular biology techniques, including, for example, chloroplast count in guard cells, examining morphological features such as leaf, flower, or pollen size (termed the *gigas* effect) and flow cytommetry.

Further as described herein, various embodiments disclosed herein utilize polyploidy induction for Rapid-breeding techniques. For example, allopolyploids may be generated from hybridization of two or more genomes followed by chromosome doubling or by fusion with unreduced gametes between or within species. For example, meiosis or mitosis takes a diploid cell and reduces it to 4 haploid cells (one copy of each gene and chromosome). However, an unreduced gamete has not undergone the reduction (e.g., by inhibiting cell division) and remains diploid. See Figures disclosed herein. In an embodiment, a method disclosed herein includes inducing at least one plant stem cell to differentiate into at least one first gamete. In an embodiment, the at least one first gamete is unreduced (i.e. has not yet undergone meiosis) such that ploidy is induced upon fertilization with a second gamete. In an embodiment, the nuclei are combined instead of the entire gamete(s).

For example, a dominant mutation coding for AGO104, a member of the ARGONAUTE family of proteins, results in formation of functional unreduced gametes. See Singh, et al., Plant Cell vol. 23: 443-458 (2011), which is incorporated herein by reference. The mutant shows defects in chromatin condensation during meiosis and subsequent failure to segregate chromosomes when screened in *Zea mays*. Id. AGO104 is needed for non-CG methylation of centromeric and knob-repeat DNA. Thus, in an embodiment, a mutant AGO104 is utilized for differentiating unreduced gametes.

In certain instances, the hybridized genomes may differ in their degree of homology such that some genomes are able to pair during mitosis and/or meiosis, while others are not. For example, in certain instances only segments of the chromosomes of the combining genomes differ (termed segmental alloploidy), and in order to achieve a "pure cross" a bridge cross, or intervening cross, may be utilized to achieve the desired hybrid.

Likewise, the multiallelic nature of loci in polyploids allows for masking deleterious alleles that may arise during modification or polyploidy induction. Further, polyploids are able to tolerate deleterious allele modifications postmutation and they have increased mutation frequency due to their large genomes. Polyploids typically have larger cells and/or plant organs than their traditional counterparts, however the larger cell volume is usually due to higher water retention, rather than an increase in biomass.

In an embodiment, the progeny are analyzed for example, by statistical sample testing of plant tissue(s) (including seeds) for further use. In an embodiment, a portion of the plant tissue(s) are utilized while maintaining the germination viability of the progeny. For example, a portion of the endosperm, zygote, embryo, blastocyst, or other seed portion may be obtained by mechanical or chemical means and utilized for analysis. For example, an automated seed sampler may be used with various embodiments disclosed herein. See for example, U.S. Pat. No. 7,941,969, which is incorporated herein by reference.

In an embodiment, the one or more desired characteristics are quantified based on the analyzed plant tissue. In an embodiment, the one or more quantified desired characteristics are compared with control plant tissue samples or known germplasm pools in order to identify frequency shifts. Likewise, DNA and RNA may be extracted from plant tissue(s) sufficient to yield DNA or RNA adequate for PCR, RT-PCR, TaqMan assays, sequencing, arrays or blots, or other amplification.

Several criteria may be established in order to determine whether additional breeding is desired. For example, a small flake from the fertilized seed (optionally retaining the embryo intact for planting, if desired) is removed for genetic analysis of a desired characteristic, whether the corresponding gene(s) are naturally occurring in the seed or artificially inserted, deleted, or mutated.

As described herein, in certain aspects a method disclosed includes molecularly modifying a plant cell. In an embodiment, a DNA construct is utilized to modify a plant cell. Assembly of DNA constructs may be done using standard methods, typically with a promoter operably coupled to the DNA, and optionally other regulatory elements such as 5' leaders, introns, 3' untranslated regions (such as polyadenylation signals), signal peptides, or repressor or enhancer sequences.

For example, promoter elements include non-constitutive promoters (such as spatially specific promoters, temporally specific promoters, inducible promoters, etc.), or constitutive promoters. For example, spatially specific promoters include organelle, cell, tissue, or organ-specific promoters functional in a plant (such as plastid-specific, root-specific, pollen-specific, or seed-specific promoter for suppressing expression of the target RNA in plastids, roots, pollen, or seeds, respectively). In an embodiment, a seed-specific, embryo-specific, gamete-specific, stem cell-specific, aleurone-specific, or endosperm-specific promoter is utilized with an embodiment. For example, temporally specific promoters can include promoters that favor promoter expression during certain developmental stages in a plant's growth or reproductive cycle, or during different times of day or night, or different seasons of the year. Inducible promoters include promoters induced by chemicals such as exogenous or synthetic chemicals as well as endogenous pheromones and other signaling molecules) or by environmental conditions such as but not limited to biotic or abiotic stress (e.g., water deficit or drought, temperature fluctuations or extremes, nutrient fluctuations or extremes, salt levels, light levels, pest or pathogen infection, or physical damage, etc.). An expression-specific promoter also includes generally constitutively expressed promoters that vary on the degree of expression.

In addition to promoter elements, in certain instances terminator elements may be utilized in the embodiments disclosed herein, including for example, polyadenylation signals as described herein. Additionally, spacer DNA segments (found, for example, between parts of a gene suppression element or between different gene suppression elements) may include translatable DNA encoding a target gene, translatable DNA encoding a marker or reporter gene, transcribable DNA derived from an intron, transcribable DNA encoding RNA that forms a structure such as a loop, stem, or aptamer capable of binding to a specific ligand, spliceable DNA including introns and self-splicing ribozymes, transcribable DNA encoding a target gene detectable by molecular biology techniques.

Promoter and enhancer elements that are active in plants include but are not limited to nopaline synthase (NOS) promoter, octopine synthase (OCS), CaMV35S promoter (cauliflower mosaic virus), rice actin promoter, maize chloroplast aldolase promoter, maize aldolase promoter, napin, maize L3 oleosin, zein Z27, globulin I, glutelin 1, peroxiredoxin antioxidant (Per 1), maize nicotianamine synthase promoter, etc. Numerous other promoters that function in plant cells (whether plant cell or another cell was the original source) may be utilized in assembling constructs for use in modifying plant cells as described herein.

Likewise, various enhancer sequences, such as 5' introns of rice actin 1 and rice actin 2 genes, maize alcohol dehydrogenase gene intron, maize heat shock protein 70 gene intron, maize shrunken 1 gene, etc. may be used to assist in increasing gene expression.

In various aspects, one or more genes or other modifications may be implemented with various embodiments disclosed herein, by for example, making multiple modifications to a single cell or by making single mutations in a cell and crossing those cells to result in a transformed plant. Such modifications may be stacked into the resulting plant with various modifications. For example, characteristics for increasing drought resistance may be stacked with characteristics for increasing yield, or tolerating herbicides. For example, transgenic plants have been produced that have demonstrated tolerance to glyphosate, dicamba, glufosinate, sulfonylurea, bromoxynil, and norflurazon, and such plants may be further modified utilizing various embodiments described herein.

Some non-limiting examples of 3' polyadenylation signals include nos 3', tml 3', tmr 3', tms 3', ocs 3', tr7 3', and others from *Agrobacterium tumefaciens* genes, heat shock protein 17 3' from wheat (*triticum aesevitum*), wheat ubiquitin gene, wheat fructose-1, 6-biphosphatase gene, rice glutelin gene, rice lactate dehydrogenase gene, rice beta-tubulin gene, pea ribulose biphosphate carboxylase gene (rbs 3'), etc.

With regard to gene suppression, various modes may be used, for example, including anti-sense, co-suppression, and RNA interference (miRNA, dsRNA, siRNA, and other forms of double stranded RNA that block translation). Several microRNA genes have been characterized in plants, including promoters for the same. See for example, U.S. Pat. No. 8,395,023, which is incorporated herein by reference. Transposable elements can also be utilized to suppress gene function. In certain instances, mutations by insertion of one or more transposable elements disrupts protein translation from a particular gene.

Modification of plant cells by transformation with molecular constructs may be used with various embodiments described herein. For example, *agrobacterium*-mediated transformation and microprojectile bombardment have been described for use with soybean, corn, wheat, rice, and sugar beet. See U.S. Pat. No. 8,410,336, which is incorporated herein by reference. Culturing conditions for transforming plant cells includes, for example, nutrient media, kept at conditions which facilitate transformation of the cells. Plant cell targets for transformation include at least one of meristem cells, calli, hypocotyls, gametes (microspores, pollen, sperm, egg, etc.), or immature embryos. In addition, callus may be differentiated from tissues such as immature embryos, hypocotyls, microspores, seedling apical meristems, etc. and can be grown into a plantlet or mature plant. Since typically not all cells are transformed when modified in this manner, one or more markers (e.g., marker genes) are generally utilized to provide an efficient system for identification of the cells that are stably transformed with DNA constructs. Further, if conferring resistance to an antibiotic or herbicide, for example, transformation may be screened by application of the antibiotic or herbicide to the plant (or plant cells).

In an embodiment, a target sequence includes at least one of amino acid catabolic genes (such as maize LKR/SDH), maize zein genes, fatty acid synthesis genes (such as plant microsomal fatty acid desaturases or plant acyl-ACP thioesterases), genes involved in multi-step biosynthesis pathways (such as genes encoding enzymes for polydydroxyalkanoate biosynthesis), genes encoding cell-cycle control proteins (such as proteins with cyclin-dependent kinase (CDK) inhibitor-like activity, genes from undesirable proteins (such as allergens or toxins), or enzymes for the biosynthesis of undesirable compounds (such as undesirable flavor or odor components). For example, a modified plant disclosed herein includes a plant with decreased allergenicty (such as peanut), regulated fruit ripening, a pest or pathogen resistant plant, or an herbicide tolerant plant.

For example, several non-limiting examples of pathogens include but are not limited to fungal, bacterial, or viral pathogens. For example, *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Pythium aphanidermatum* and other *Pythium* spp., *Rhizoctonia solani, Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglutinans* (*F. subglutinans*), *Diplodia maydis, Sporisorium holci-sorghi, Colletotrichum graminicola, Setosphaeria turcica, Aureobasidium zeae, Phytophthora infestans, Phytophthora sojae, Sclerotinia sclerotiorum, Pseudomonas avenae, Pseudomonas andropogonis, Erwinia stewartii, Pseudomonas syringae* pv. *syringae*, maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), etc. See for example, U.S. Pat. No. 8,395,023, which is incorporated herein by reference.

For example, several non-limiting examples of pests capable of destroying plants include but are not limited to northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape *colaspis* (*Colaspis brunnea*), seedcorn beetle (*Stenolophus lecontei*), and slender seedcorn beetle (*Clivinia impressifrons*), as well as parasitic nematodes. Id.

For example, several non-limiting examples of target genes related to pests include but are not limited to major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, etc. Id.

In an embodiment, modification of plant cells is conducted with one or more aptamers, which include DNA or RNA sequences that recognize and specifically bind to a particular ligand or molecule, often with high affinity. Aptamers have been utilized similarly to antibodies for binding specific antigens or receptors as well as for protein antagonists, as molecular escorts for delivery of an agent to a particular cell or tissue, as well as part of a riboswitch. Riboswitches include complex folded RNA sequences that contain an aptamer domain for a specific ligand and can operate as "cis" or "trans" elements. Cis riboswitches may control gene expression by harnessing allosteric structural changes caused by ligand binding, whereas trans riboswitches control expression not operably linked to the riboswitch itself. For example, a riboswitch defaults to "on" position during gene expression, and the riboswitch is turned to the "off" position when an increased concentration of the ligand is bound by the aptamer domain of the riboswitch and the riboswitch terminates transcription or translation of the gene under its control. Thus, in certain embodiments described herein, plant cells are modified and may result in stable transgenic plants as determined by the ligand being bound to an aptamer and the resulting expression or suppression of a target sequence.

Another class of RNA apatamers useful with an embodiment disclosed herein include "thermoswitches" which do not bind a ligand but that determine the aptamer's conformation by temperature, so as to be thermally responsive.

In an embodiment, modifying plant cells to reduce damage caused by disease or pest includes a transgene that transcribes to an RNA aptamer capable of binding to a ligand that is at least part of a molecule endogenous to the pest or pathogen source of the disease or destruction. In this way, binding to the ligand reduces damage to the plant relative to a plant without the transgene. In an embodiment, the transgene includes at least partial sequence of a gene found in a pathogen or in the gut of a pest.

In an embodiment, a target sequence includes a gene native to the particular plant utilized in various embodiments disclosed herein, a transgene in a transgenic plant, a gene native to a pest or pathogen, etc. For example, plant cells modified as described herein may be modified to provide resistance to a particular disease or pest. In order to convey such resistance, a gene native to the particular causal agent may be incorporated into the plant when modified as disclosed in various embodiments herein. Alternatively, in another example, multiple copies of a native gene to the plant may be incorporated, for example, to increase yield or nutritional content. A target sequence includes a sequence that expresses a specific gene or a sequence that suppresses a specific gene. Moreover, the target sequence includes a translatable sequence (coding sequence) or a non-coding sequence (non-coding regulatory sequence), or both. The target sequence includes sequences from the plant itself, its species, or another species including any eukaryote or prokaryote, depending on the desired characteristic.

In an embodiment, regulatory RNA is utilized to modify plant cells as described herein, and include ribozymes (self-cleaving ribozymes, hammerhead ribozymes, hairpin ribozymes, etc.) and may include sense or anti-sense segments capable of hybridizing to form an intramolecular double-stranded RNA.

In an embodiment, clustered regularly interspersed short palindromic repeats (CRISPR) is utilized for the one or more modifications of plant cells for Rapid-breeding of plants as described. See van der Oost, Science, (2013) pp. 768-770, vol. 339; and Mali et al., Science (2013), pp. 823-826, vol. 339; and Cong et al., Science (2013), pp. 819-823, vol. 339; each of which is hereby incorporated by reference. For example, CRISPR utilizes RNA-guided DNA nuclease for highly specific gene targeting (e.g. for modification of genes). Id. For example, precise genome engineering may be conducted based on the RNA-guided Cas9 nuclease, and can be utilized for multiple gene recognition sites. Id.

For example, in an embodiment CRISPR is utilized for targeting based on Watson-Crick complementarity, and in an embodiment CRISPR machinery can be reprogrammed to target a different DNA sequence through the use of a different crRNA. In an embodiment, CRISPR is utilized for targeting a complementary 24-48 RNA sequence, with little to no mismatches.

As described herein, plant stem cells are utilized in various embodiments disclosed. However, various other plant cells may be utilized from the resulting plant generated by methods disclosed herein, or in the process of generating the resulting plant. In this regard, plants may be crossed by modifying one gamete or nucleus and not the second gamete or nucleus utilized in sexual fertilization of the new progeny. In certain aspects, markers associated with one gamete, nucleus, or modification (e.g., gene modification) are utilized with various embodiments disclosed herein. For example, a selectable marker may be linked to a DNA construct, a marker for herbicide tolerance may be tested by application of the herbicide to the progeny plant, or antibiotic resistance may serve as a marker for stable integration of a construct in the plant cell.

Transformation of DNA constructs into plant cells is likely to result in a percentage of target plant cells that do not receive the construct or achieve expression of the construct. Common selective marker genes include those that confer resistance to antibiotics such as kanamycin and paromomycin, hygromycin B, spectinomycin, gentamycin, for example, or resistance to herbicides such as glufosinate, dicamba, or glyphosate. As with animal cells, markers such as green fluorescent protein or luciferase may be employed to indicate that gene expression from the construct is occurring, or for example, a gene expressing beta-glucuronidase or uidA gene may be utilized, in conjunction with chromogenic substrates to visually screen modified plant cells.

As described herein, if plant cells are modified as part of various embodiments disclosed, subsequent to fertilization occurs and the resulting progeny plant seed is obtained, the seed may be tested or optionally cultured to a plantlet stage and then tested. In the case where the fertilized seed is tested, in an embodiment a portion of the endosperm is removed for analysis without disrupting the embryo of the seed. In an embodiment, a portion of the embryo is analyzed without disrupting the viability of the embryo. In an embodiment, a small portion of the fertilized seed is analyzed without disrupting the viability of the embryo.

As described herein, an optional step in various embodiments disclosed include culturing the progeny seed under conditions that allow for the seed to grow to multiple cells, to a plantlet stage, or to a mature plant. Plant seeds that have been modified, in certain embodiments, grow to plants that have an improved characteristic as compared with a control plant. As described herein, modified seeds or plants with improved characteristics are selected by evaluating the seeds or plants at a microscopic, molecular, genotype, or phenotype level.

In other embodiments, the seed and or plant generated by various embodiments disclosed herein harbor naturally occurring improvements over control plants, and such improved seeds or plants are derived by the Rapid-breeding processes disclosed. Improvements include, for example, higher seed quality, better water efficiency, better nutrient efficiency, greater temperature tolerance, higher yield, increased seed protein, or increased seed oil, level of fermentable starch, increased metabolite, level of fatty acids, level of amino acids or proteins, as well as other characteristics described herein.

As described herein, the progeny of various embodiments disclosed herein may be analyzed by various means, including, for example, microscopic or molecular analysis. In addition to the molecular or microscopic analysis of the progeny seeds or plants, in certain aspects where the seeds are grown to plantet or mature plant stage, several screening assays may be utilized, depending on the characteristic desired to be analyzed. For example, plantlets or mature plants may be screened in greenhouses or field trial or research centers, and may include detecting changes in morphology of the plant, physiological characteristics, biomass, or chemical composition. For example, chemical composition of the progeny seeds or plants may be analyzed by evaluating seed composition for protein, free amino acids, oil, free fatty acids, starch, tocopherols, and other components. For example, biomass may be measured by evaluating plant height, stem diameter, root and shoot weights, leaf or shoot lengths or diameters, etc., whereas plant morphology may be evaluated by screening for days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness or prolificacy, green snap, pest resistance, kernals per row, number of rows of kernals on an ear, kernel abortion, kernel weight, kernel size, kernel density, physical grain quality, bushiness, height, thicker or narrower leaves, striped leaves, knotted trait, chlorosis, albino, anthocyanin production, altered tassels, altered ears, altered roots, or similar characteristics. As described herein, in addition to molecular or microscopic/cellular analysis, seeds or plants can be analyzed by testing against stress conditions, such as water use efficiency, enhanced cold tolerance, shade tolerance, herbicide resistance, etc., by growing plants/plantlets under the stress condition to be analyzed and evaluating the response against control plants/plantlets.

For example, marker-assisted selection (MAS) relies on quantitative trait loci (QTL) studies derived from the analysis of a few segregating populations and may be employed for the analysis as described herein with regard to several claimed embodiments. Likewise, genomic selection relies on phenotyping and high-density genotyping of a sufficiently large and representative sample of the population, with the majority of loci regulating a quantitative trait in linkage disequilibrium with one or more molecular markers. See, for example, Resende, et al., New Phytologist (2012)

193: 617-624, which is incorporated herein by reference. In certain embodiments, the MAS or genomic selection is utilized on a very early plant (zygote, blastocyst, embryo, etc.), while in certain other embodiments the MAS or genomic selection is utilized at a plantlet or mature plant stage. For example, age and genotype×environment interaction affect expression of certain complex genetic characteristics, and need a more mature plant in order to accurately measure such characteristics. Likewise, for certain characteristics that are expressed in the early plant, simple molecular testing of particular markers at the early plant stage are sufficient for establishing presence or absence of the trait. As described herein, in certain plants the time-frame between the beginning of breeding and the production of improved seeds can span multiple decades. Id. Thus, in an embodiment, the techniques of MAS and genomic selection may be employed with certain embodiments disclosed herein for Rapid-breeding methods.

In an embodiment, one or more QTLs are linked with at least one of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, increased consumer appeal, industrial use characteristics, or other characteristics as described herein. In an embodiment, one or more progeny are selected based on at least one characteristic indicative of a recurrent parent that assists in selection for marker-assisted backcrossing.

In an embodiment, additional transcription factors for use in various embodiments disclosed, or additional genes of interest associated with desired characteristics may be derived by techniques, such as differential screening using, for example, subtractive hybridization of a cDNA library, PCR, RT-PCR, Northern blot, Reverse Northern blot, Southern blot, Western blot, DNA fingerprinting, dot-blots, new generation sequencing, gene cloning or Random Primed RT-PCR, etc. readily assists in identification of genes or proteins of interest in eukaryotic cells, including plants.

For example, the genomes of many different plant varieties have been sequenced in full or in large part, thus enabling ready identification of particular genes or proteins as determined by differential screening related to various cell types, for example. In an embodiment, a differential screening for a particular plant is conducted with at least two or more of a gametophyte, gamete, spore, or sporophyte. In an embodiment, a differential screening is conducted between a male gamete and a female gamete of the same species. In an embodiment, the differential screening is conducted between related but different species, or related but different cultivars, in order to more readily identify the genes or proteins more intricately involved in differentiation of different cell types. In an embodiment, identification of a homolog is sufficient for utilization in differentiation of a cell type or development of a sufficient factor therefor.

For example, genomic sequence information for rice, maize, cucumber, oilseed, legumes, cocoa, *eucalyptus*, wild strawberry, apple, grape, tomato, potato, wheat, barley, banana, *cannabis*, grasses, and other crops and trees have been obtained in whole or in large part. With new generation sequencing, the relevant sequence information of other plants is readily identifiable.

As illustrated in FIG. 1, an embodiment includes a method 100 for Rapid-breeding of plants. As illustrated, cells (stem cells, gametophytes, sporophytes, somatic cells, etc.) are extracted 105 from Parent 1 and Parent 2 and induced to differentiate in vitro tissue culture 110, deriving gametes or transferable nuclei 115 that when combined 120, give rise to one or more zygote progeny 185. Next, the progeny are analyzed 130 as described herein utilizing cell, molecular, or microscopic methods, for example, or optionally cultured 125 to give rise to more than one cell. As illustrated, if the progeny are optionally cultured 125, they may be subsequently analyzed 130 for example, by removing a small portion of plant tissue or clonal cells to evaluate the genotype as described herein. Following analysis of the progeny 130, the progeny are selected 135 based on the analysis. Optionally, the selected progeny may be cultured 125, or cultivated 140 to plantlet stage or optionally to mature plant stage 150. Alternatively, following selection 135 of the progeny based on the analysis, the progeny cells (which include multipotent, pluripotent, and/or totipotent cells) are utilized to repeat 195 the Rapid-breeding process. Optionally, cultured plant cells 125, cultivated plantlets 140 or cultivated mature plants 150 may be optionally validated through a second analysis 145 following the growth in culture or through cultivation. Cells may be obtained from progeny at any step following analysis for one or more desired characteristics, as illustrated in FIG. 1. For example, in an embodiment, culturing plant cells or plant progeny includes growing them in a tissue culture plate. In an embodiment, cultivating a plant includes growing the progeny or other plants in a greenhouse, field, test plot, or small plant containers located indoors or outdoors.

Figure 2:
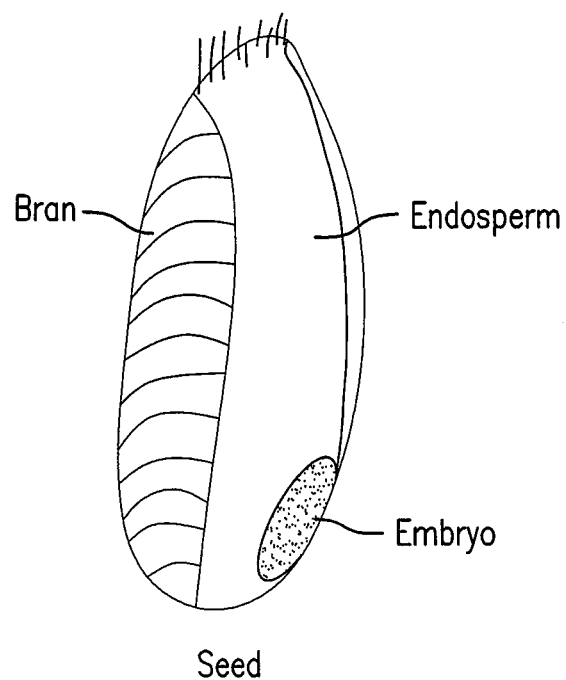
FIG. 2 illustrates a partial view of a seed.

As illustrated in FIG. 2, in an embodiment, a portion of the plant tissue (such as a seed) is removed for analysis as described herein. In an embodiment, a portion of the endosperm is removed for analysis, leaving the embryo intact and maintaining the germination viability of the seed. In an embodiment, the endosperm and embryo are derived from sperm that share the same genotype, thus eliminating possible variation in inheritance from the sperm fertilizing the polar body that gives rise to the endosperm and the sperm fertilizing the egg that gives rise to the embryo.

Figure 3:
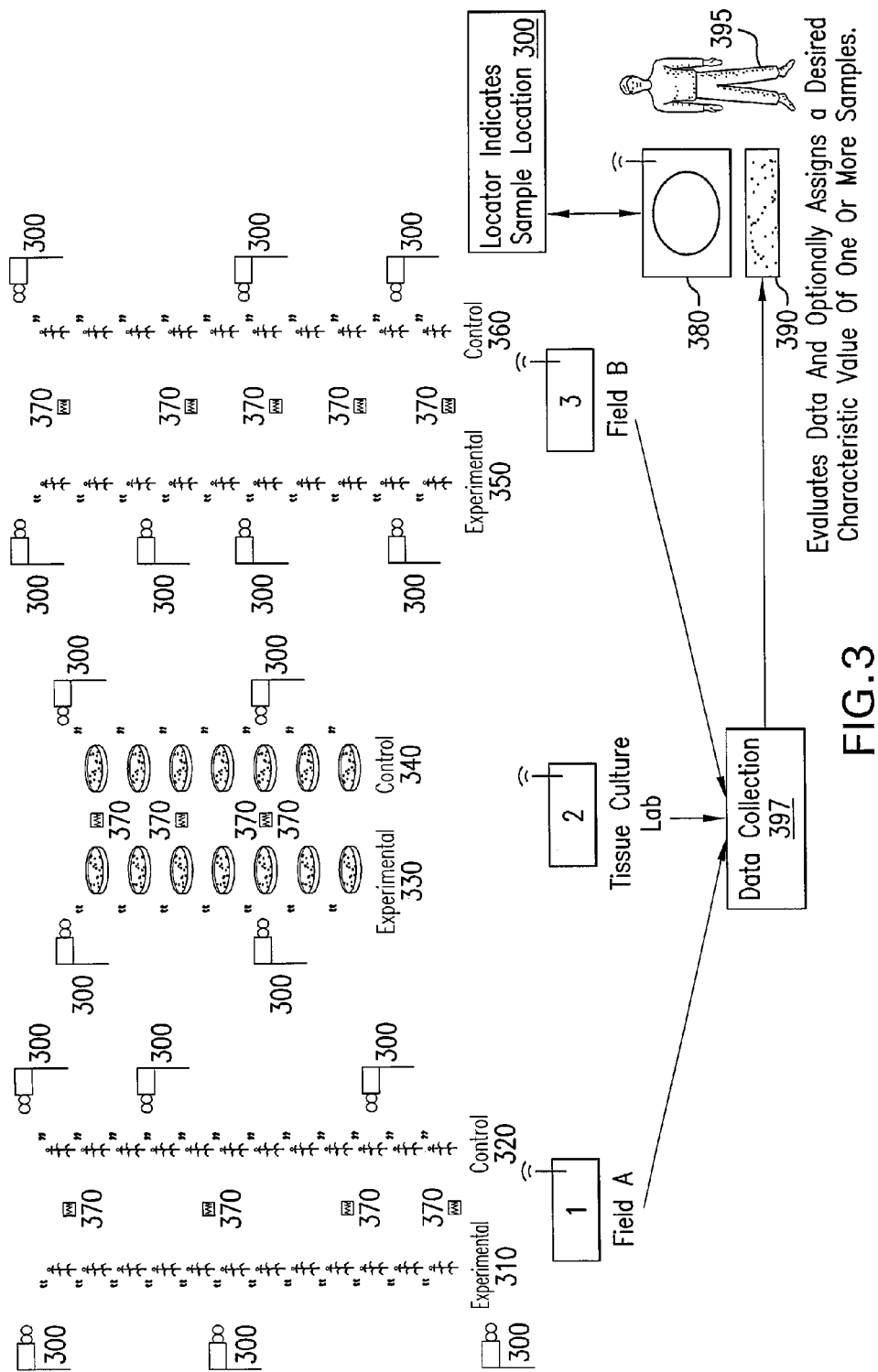
FIG. 3 illustrates a partial view of an embodiment disclosed herein.
Figure 4:
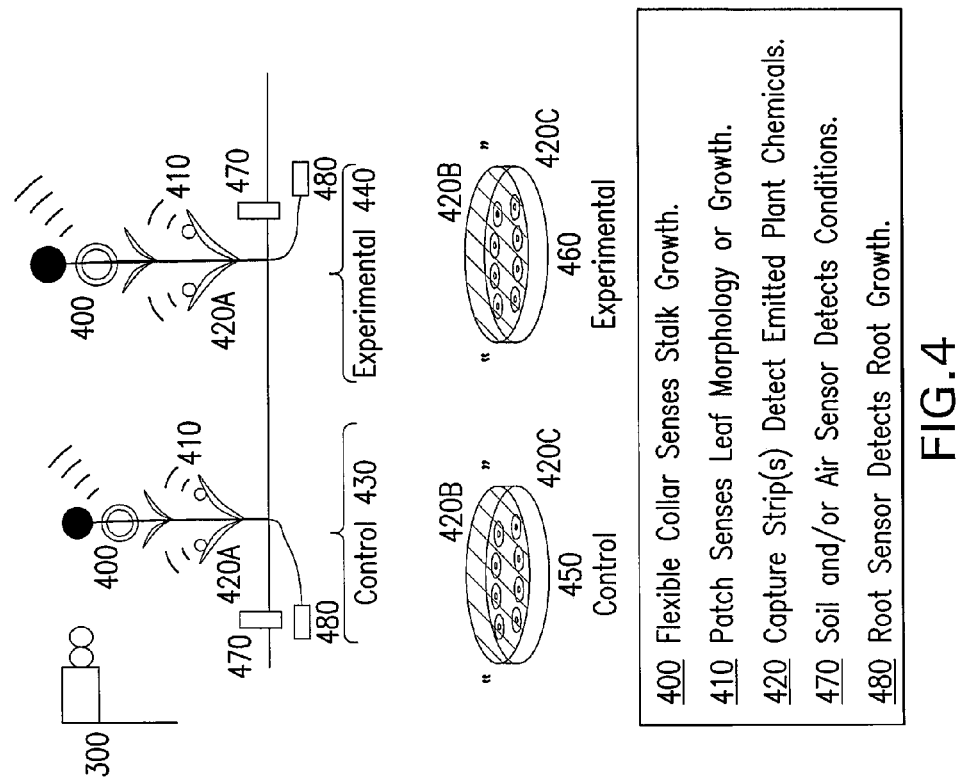
FIG. 4 illustrates a partial view of an embodiment disclosed herein.
Figure 7:
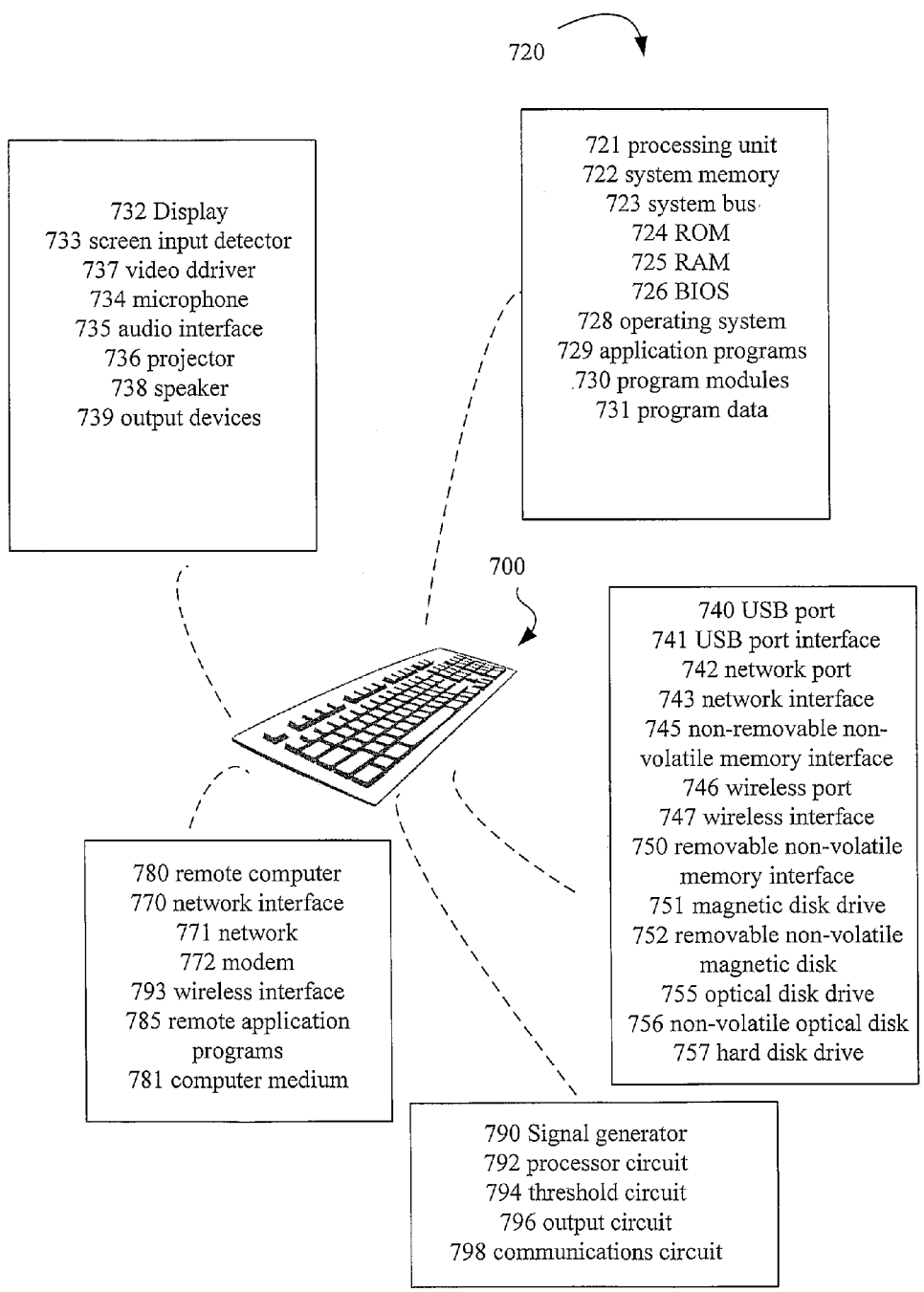
FIG. 7 illustrates a partial view of an embodiment disclosed herein.

As illustrated in FIG. 3, in an embodiment, the progeny generated from the rapid-breeding disclosed herein are analyzed genetically (including genotypically, for example) or epigenetically, as described herein, and further analyzed phenotypically in tissue culture plates, or as plantlets/plants in a greenhouse or field. As illustrated in FIG. 3, one or more cameras 300 are utilized to survey a plot, a row, or a specific plant/dish, while a location marker (e.g., global positioning system indicator, etc.) 370 is placed at various positions around or near the growing plants/plant cells. As described herein, the cameras include one or more of infrared cameras, visual cameras, x-ray cameras, or similar. Information detected from these or other sensors are transmitted (optionally wirelessly) to a central database, as indicated by "1," "2," or "3," and the data collected 397 is evaluated by a user that is a person 395, or computer 380, for example. The user evaluates the data and optionally enters additional observed data via an input/output device 390. Based on the data evaluation, a Desired Characteristic Value from one or more samples is assigned, and any experimental progeny (310, 330, 350, etc.) that include desired characteristics may be assessed further. Likewise, any experimental progeny that lack the desired characteristics, or that bear a phenotype no better than the control progeny (320, 340, 360, etc.) may be culled from further research. In an embodiment, a locator indicator 398 is utilized to locate a particular progeny for further assessment or for culling based at least in part on the location marker 370 in the field or greenhouse. In an embodiment, for example, the location marker 370 includes a transmitter, and the location indicator 398 includes a receiver. In an embodiment, for example, the location marker 370 includes a receiver, and the location indicator 398 includes a transmitter. In an embodiment, one or more components described in FIG. 7 are implemented in FIG. 3. In an embodiment, an integrated sensor-to-database collection may be utilized, such as a wireless sensor network, for example that integrates collected information, optionally encrypts information shared wirelessly and optionally through an internet interface. See Bencini et al., intechopen pp. 1-18, which is incorporated herein by reference. In an embodiment, the information contributes to and/or compares the information with a database. In an embodiment, the database includes genomic sequence information for the particular As illustrated in FIG. 4, included in the analysis of the progeny of the rapid-breeding disclosed herein, the phenotype may be assessed by utilizing one or more sensors, for example, that contact the plant or plant cells, or are in the vicinity of the plant or plant cells. In an embodiment, the one or more sensors include at least one of a receiver or transmitter. In an example, the sensors detect particular environmental conditions or plant/plant cell conditions and transmit the information to a user (as shown in FIG. 3) where the information is collected and/or evaluated. In an embodiment, as described in FIG. 3, one or more progeny are culled or further assessed depending on the information collected or evaluated from the one or more sensors.

For example, a collar 400 includes a flexible band with a force sensor or strain sensor incorporated that senses stalk diameter may be utilized for sensing plant growth. In an embodiment, the collar 400, is in a fixed state and erupts or breaks apart as the plant reaches a threshold size, wherein the breaking of the collar sends a signal. In an embodiment, a sensor in the form of a patch 410 is attached to a leaf and is capable of measuring leaf morphology or growth. In an embodiment, a capture strip 420A or B is utilized for detecting emitted plant chemicals, such as carbon dioxide, oxygen, pheromones, stress hormones, reactive oxygen species, and others. In an embodiment, the capture strip 420A is located on the plant or plant cells. In an embodiment, the capture strip is located in the vicinity of the plant or plant cells, and may include, for example, the cover 420B to a tissue culture dish or 420C the floor of the tissue culture plate. For example, a colorimetric oxygen sensor, or other gas sensor may be employed with the tissue culture dishes. In another example, a pH indicator or nutrient indicator is employed that includes a transmitter or receiver in order to share information relating to the tissue culture plates. In another embodiment (not shown), remote spectral sensing is employed that includes sharing of information or evaluating the information against a data base, as described herein. For example, remote spectral sensing of crops has been utilized through imagery of a field or plot, where the incident electromagnetic radiation is generally sunlight. See Li et al., Electrochem. Soc. Winter 2010, pp. 41-46, which is incorporated herein by reference. For example, measuring sunlight of the crop and soil that is reflected, absorbed, and/or transmitted depending on the wavelength and the surface it strikes, indicates differences in physical or chemical properties of the crops, e.g., leaf color, texture, shape, etc. In an embodiment, the spectral reflectance measurements are utilized for analysis, including the ratio of reflected energy to incident energy as a function of wavelength, and can be evaluated based on spatial or temporal resolution. In an embodiment, one or more of a spectrometer, radiometer, or digital camera may be mounted on a variety of platforms either on the ground, aerial, or space to gather data. Id.

In an embodiment, one or more sensors include soil and/or air sensors 470 that detect environmental conditions. In an embodiment, one or more root sensors 480 are banded on the plant roots with a strain sensor or threshold sensor as described for the plant stalk, or set at a goal distance for root growth to approach and provide a signal. In an embodiment, one or more cameras 300 are placed on or near the vicinity of the plants or plant cells in order to gather visual information about the plants or plant cells. As described in FIG. 3, the cameras include one or more of infrared cameras, visual cameras, x-ray cameras, or similar.

In an embodiment, one or more sensors including Raman and Fourier Transform Infrared spectroscopy, capacitance probes, reflectometers, ultrasonic ranging sensors, pH soil-based sensors, Eddy covariance sensors, fluorescence-based optical sensor, optical or microwave sensors, or other sensors may be employed in certain embodiments. See Pajares, Sensors (2011) 11:8930-8932, which is incorporated herein by reference.

In an embodiment, one or more "smart transducers" are utilized with certain embodiments disclosed. Specifically, "smart transducers" include sensors or actuators equipped with microcontrollers to provide local "intelligence" and network capability and can combine sensing, computing, and communication. See Wang et al., Comp. and Elect. In Ag. (2006) 50: 1-14, which is incorporated herein by reference.

In an embodiment, a system disclosed herein includes a network of research stations or plant testing stations that are configured to share information regarding the one or more measured characteristics of the plantlet or mature plant developed according to methods described herein. In an embodiment, the network of stations includes means to transmit and/or receive information regarding the one or more measured characteristics of the plantlet or mature plant developed according to methods described herein.

Figure 5:
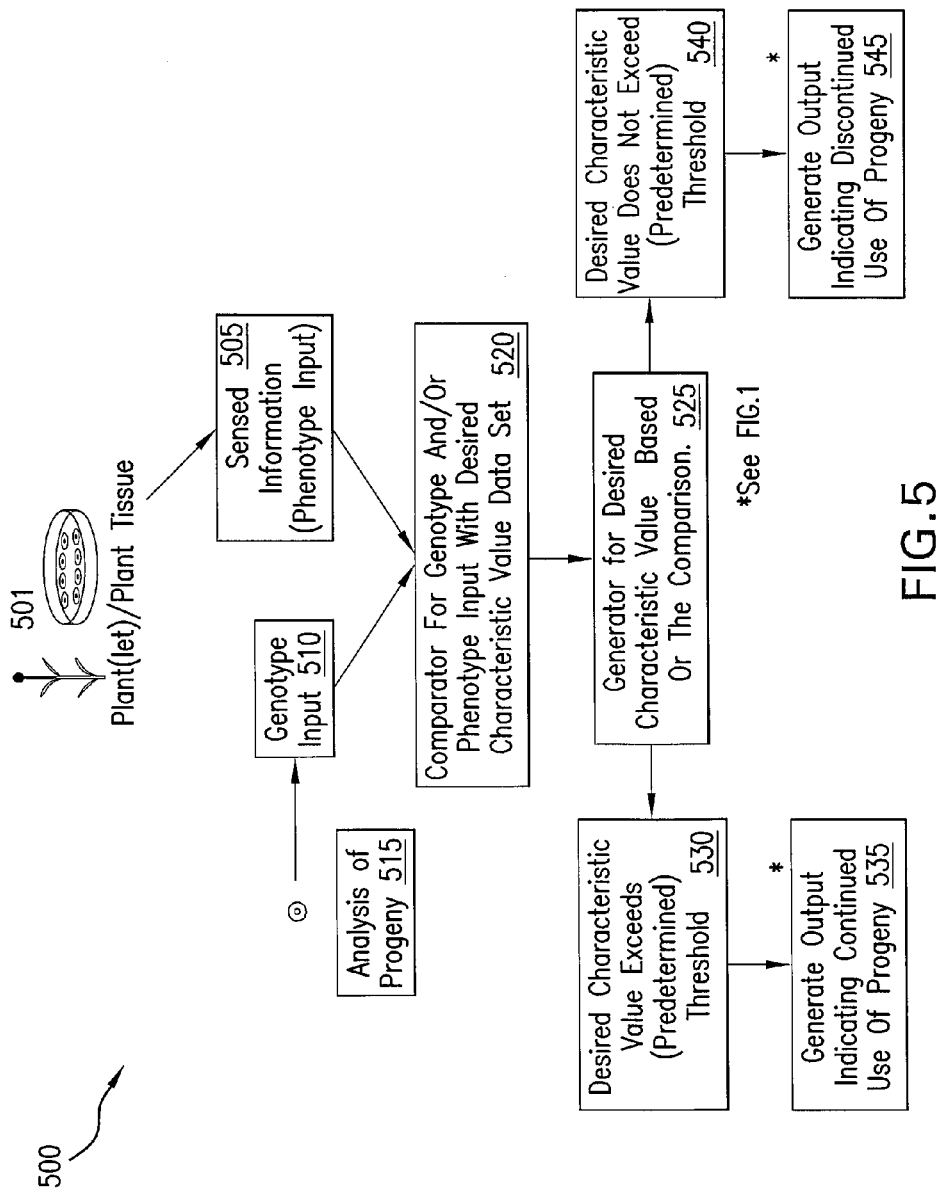
FIG. 5 illustrates a partial view of an embodiment disclosed herein.

As described in FIG. 5, a system or method 500 includes culturing or cultivating the progeny 501 of the rapid-breeding process, and analyzing the progeny 515. In an embodiment, genotype information is obtained from the progeny and input 510 into the system. In an embodiment, sensed information as described herein, relating to phenotype 505 is input into the system. Utilizing the input information, next a comparator for the genotype and/or phenotype input is employed with a Desired Characteristic Value dataset 520. In an embodiment, the comparator is operably coupled to a database related to one or more of at least one parent plant of the progeny tested, or other progeny of a breeding cycle with at least one parent in common as the progeny tested. In an embodiment, the database is related to progeny of an earlier breeding cycle as the progeny tested. In an embodiment, the database is related to progeny of a later breeding cycle as the progeny tested (for example, when the progeny tested was allowed to grow for a length of time that surpassed the amount of time needed for at least one additional breeding cycle). In an embodiment, a generator for the Desired Characteristic Value 525 is employed based on the comparison. From the generated Desired Characteristic Value, in an embodiment, the Desired Characteristic Value exceeds a (optionally predetermined) threshold value 530 and an output is generated indicating that the progeny should be continued to be used in the process 535 (e.g., allowed to grow further or be subjected to further analysis). In an embodiment, the Desired Characteristic Value does not exceed a (optionally predetermined) threshold 540 such that an output is generated indicating that the progeny should be discontinued from the process (e.g., culled from the group). See for example, FIG. 1. In an embodiment, one round of fertilization are performed, and the progeny are from that first round of fertilization. In an embodiment, multiple rounds of fertilization are performed, and the progeny from one or more of the second, third, fourth, fifth, sixth, seventh, eighth, ninth, tenth, or more round.

For example, a sensed response for a particular progeny being tested generates a Desired Characteristic Value dataset (or a starting dataset is derived from "ideal" Desired Characteristic Values based on quantification of genotype and phenotype characteristics). Based on the queries of the database from further sensors reporting additional information regarding the progeny, the Desired Characteristic Value may increase or decrease as time goes on. Further as described, such database generation or inquiry may occur in real-time, and may provide feedback in the form of an output or other information. For example, as described, once a progeny exceeds a particular threshold, an alert is generated in the form of an output (e.g., visual, audio, tactile, etc.) indicating that the threshold has been exceeded and the progeny should continue to be used in the process. Additionally, any change itself in the Desired Characteristic Value may be alerted as to whether the change has exceeded a threshold (optionally predetermined) for a particularly exuberant progeny. As indicated, in an embodiment, the Desired Characteristic Value (DCV) dataset may be derived from various sources, and may evolve with additional queries or inputs. See for example, FIGS. 5 and 6. In this way, the progeny may be evaluated phenotypically, as well as genotypically or epigenetically, over time. As described, the first analysis of progeny is conducted very early following fertilization, and optionally progeny are selected for culturing in the lab or cultivating in a greenhouse or field. Thus, in an embodiment the DCV is dynamic, and the first input related to the DCV may include the first genotyping or other analysis of the progeny very early following fertilization, and this information may be maintained over time either as stored information or for use with comparison for other progeny being tested. As indicated herein, any number of steps in the various disclosed rapid-breeding embodiments may be automated. For example, shortly after fertilization when the first analysis is conducted on the progeny, several progeny show positive genotypes for a particular desired characteristic and may start out with a high Desired Characteristic Value. Next, the positive genotype progeny are selected for further culturing and over time additional positive or negative phenotypic or epigenetic changes occur that increase or decrease the progeny's Desired Characteristic Value depending on the "ideal" desired characteristic. Thus, the various characteristics of the progeny may be quantified and compared in order to determine the Desired Characteristic Value over time.

Figure 6:
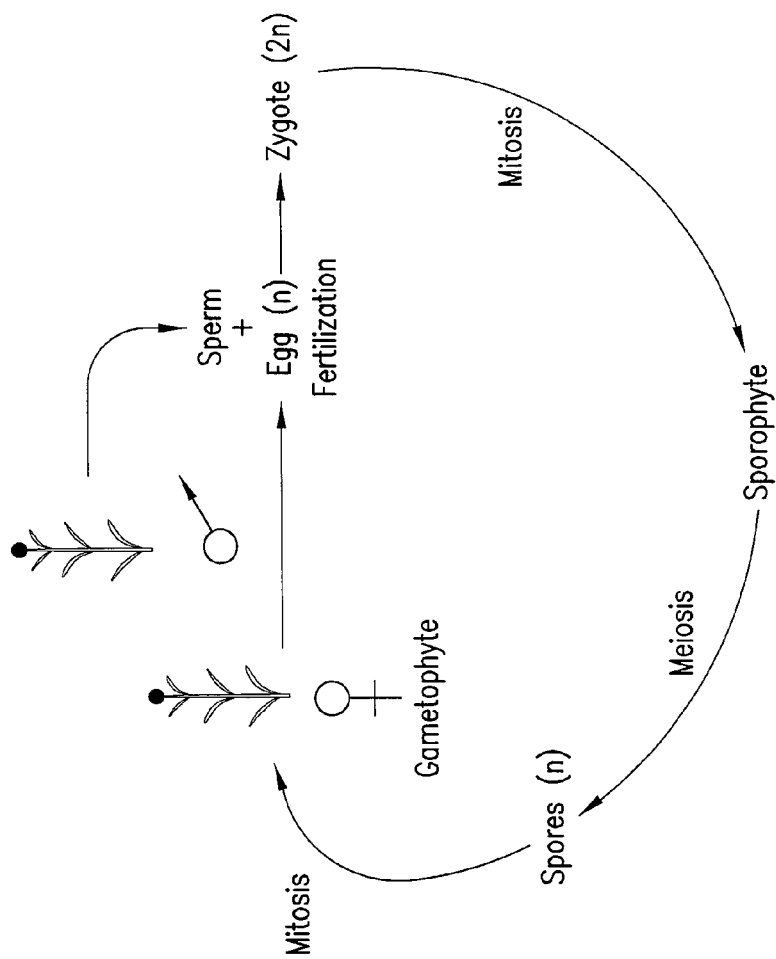
FIG. 6 illustrates a partial view of a sexual reproduction cycle in plants.

As illustrated in FIG. 6, sexual reproduction in plants involves meiosis and mitosis, for example, when gametophytes give rise to sperm (haploid) or egg (haploid) cells. When fertilization occurs, and the male sperm and female egg cells are combined, the resulting zygote (diploid) undergoes mitosis, producing a sporophyte, which in turn undergoes meiosis to produce spores (haploid) that undergo mitosis to produce the gametophyte. As described herein, certain rapid-breeding embodiments bypasses various portions of this process and as a result, increases the efficiency and effectiveness of plant breeding.

As described herein, FIG. 7 illustrates an input/output device 700 operably coupled with a computing device 720 that includes a processing unit 721, a system memory 722, and a system bus 723 that couples various system components including the system memory 722 to the processing unit 721. The system bus 723 may be any of several types of bus structures including a memory bus or memory controller, a peripheral bus, and a local bus using any of a variety of bus architectures. The system bus 723 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The system memory includes read-only memory (ROM) 724 and random access memory (RAM) 725. A basic input/output system (BIOS) 726, containing the basic routines that help to transfer information between sub-components within the thin computing device 720, such as during start-up, is stored in the ROM 724. A number of program modules may be stored in the ROM 724 or RAM 725, including an operating system 728, one or more application programs 729, other program modules 730 and program data 731.

A user may enter commands and information into the computing device 720 through input devices, such as a number of switches and buttons, illustrated as hardware buttons 744, connected to the system via a suitable interface 745. Input devices may further include a touch-sensitive display with suitable input detection circuitry, illustrated as a display 732 and screen input detector 733. The output circuitry of the touch-sensitive display 732 is connected to the system bus 723 via a video driver 737. Other input devices may include a microphone 734 connected through a suitable audio interface 735, and a physical hardware keyboard (not shown). Output devices may include at least one the display 732, or a projector display 736.

In addition to the display 732, the computing device 720 may include other peripheral output devices, such as at least one speaker 738. Other external input or output devices 739, such as a joystick, game pad, satellite dish, scanner or the like may be connected to the processing unit 721 through a USB port 740 and USB port interface 741, to the system bus 723. Alternatively, the other external input and output devices 739 may be connected by other interfaces, such as a parallel port, game port or other port. The computing device 720 may further include or be capable of connecting to a flash card memory (not shown) through an appropriate connection port (not shown). The computing device 720 may further include or be capable of connecting with a network through a network port 742 and network interface 743, and through wireless port 746 and corresponding wireless interface 747 may be provided to facilitate communication with other peripheral devices, including other computers, printers, and so on (not shown). It will be appreciated that the various components and connections shown are examples and other components and means of establishing communication links may be used.

The computing device 720 may be designed to include a user interface. The user interface may include a character, a key-based, or another user data input via the touch sensitive display 732. The user interface may include using a stylus (not shown). Moreover, the user interface is not limited to an actual touch-sensitive panel arranged for directly receiving input, but may alternatively or in addition respond to another input device such as the microphone 734. For example, spoken words may be received at the microphone 734 and recognized. Alternatively, the computing device 720 may be designed to include a user interface having a physical keyboard (not shown).

In certain instances, one or more components of the computing device 720 may be deemed not necessary and omitted. In other instances, one or more other components may be deemed necessary and added to the computing device.

In certain instances, the computing system typically includes a variety of computer-readable media products. Computer-readable media may include any media that can be accessed by the computing device 720 and include both volatile and nonvolatile media, removable and non-removable media. By way of example, and not of limitation, computer-readable media may include computer storage media. By way of further example, and not of limitation, computer-readable media may include a communication media.

Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 720. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

The computing device 720 may also include other removable/non-removable, volatile/nonvolatile computer storage media products. For example, such media includes a non-removable non-volatile memory interface (hard disk interface) 745 reads from and writes for example to non-removable, non-volatile magnetic media, or a removable non-volatile memory interface 750 that, for example, is coupled to a magnetic disk drive 751 that reads from and writes to a removable, non-volatile magnetic disk 752, or is coupled to an optical disk drive 755 that reads from and writes to a removable, non-volatile optical disk 756, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 757 is typically connected to the system bus 723 through a non-removable memory interface, such as the interface 745, and magnetic disk drive 751 and optical disk drive 755 are typically connected to the system bus 723 by a removable non-volatile memory interface, such as interface 750.

The drives and their associated computer storage media discussed above provide storage of computer-readable instructions, data structures, program modules, and other data for the computing device 720.

A user may enter commands and information into the computing device 720 through input devices such as a microphone, keyboard, or pointing device, commonly referred to as a mouse, trackball, or touch pad. Other input devices (not shown) may include at least one of a touch sensitive display, joystick, game pad, satellite dish, and scanner. These and other input devices are often connected to the processing unit through a user input interface that is coupled to the system bus, but may be connected by other interface and bus structures, such as a parallel port, game port, or a universal serial bus (USB).

The computing system may operate in a networked environment using logical connections to one or more remote computers, such as a remote computer 780. The remote computer 780 may be a personal computer, a server, a router, a network PC, a peer device, or other common network node, and typically includes many or all of the elements described above relative to the computing device 720, although only a memory storage device. The network logical connections include a local area network (LAN) and a wide area network (WAN), and may also include other networks such as a personal area network (PAN) (not shown). Such networking environments are commonplace in offices, enterprise-wide computer networks, intranets, and the Internet. Included herein is a network for field research station(s).

When used in a networking environment, the computing system is connected to the network 771 through a network interface, such as the network interface 770, the modem 772, or the wireless interface 793. The network may include a LAN network environment, or a WAN network environment, such as the Internet. In a networked environment, program modules depicted relative to the computing device 720, or portions thereof, may be stored in a remote memory storage device. By way of example, and not limitation, remote application programs 785 as residing on computer medium 781. It will be appreciated that the network connections shown are examples and other means of establishing communication link between the computers may be used.

In certain instances, one or more elements of the computing device 720 may be deemed not necessary and omitted. In other instances, one or more other components may be deemed necessary and added to the computing device 720.

The signal generator 790 includes a signal generator configured to generate a signal indicative of the desired characteristic of the plant or plant tissue. In one embodiment, the signal may include a raw data signal, i.e., a capacitance measurement, a change in one or more measurements of a phenotypic characteristic, or an indicator that a desired characteristic has exceeded a (predetermined) threshold. In one embodiment, the signal generator may include a processor circuit 792, a threshold circuit 794, an output circuit 796, or a communications circuit 798. In one embodiment, the communications circuit may be operable to communicate using an electrical conductor or using a wireless transmission. In one embodiment, the signal generator may include an instance of the thin computing device 720 and the processor circuit may be the processing unit 721.

In one embodiment, the system actively monitors (e.g., detects, tracks, etc.) a plant or plant tissue located by using at least one of computerized axial tomography, fiber optic thermometry, infrared thermography, magnetic resonance imaging, magnetic resonance spectroscopy, microwave thermography, microwave dielectric spectroscopy, positron emission tomography, ultrasound reflectometry, spectroscopic imaging, visual imaging, infrared imaging, single photon emission computed tomography, global positioning system, satellite imaging, or the like.

PROPHETIC EXAMPLES

Example 1: Cycling of Gametes In Vitro (CoGiV)

1. Producing Pluripotent Plant Stem Cells In Vitro.

Plant cell explants are cultured in vitro (dedifferentiated) to generate callus cells which contain pluripotent plant stem cells. Plant pluripotent stem cells may be obtained from in vitro plant tissue cell cultures which are initiated from somatic or embryonic tissues. For example, a leaf tissue explant, of approximately 1 cm2, is cultured on solid media (containing agar) which contains essential salts, vitamins and hormones. The media contain plant hormones, auxins (e.g., 2,4 dichlorophenoxyacetic acid (2,4-D)) and cytokinins known to induce growth of a callus which is comprised of pluripotent stem cells (see e.g., He et al., PLoS Genetics 8: e1002911. doi:10.1371/journal.pgen.1002911 and Plant Cell and Tissue Culture, p. 3-15, Indra K. Vasil, Trevor A. Thorpe (eds.), 1994 Kluwer Acad. Publ., Dordrecht, The Netherlands, each of which is incorporated herein by reference). Callus cells which arise in culture are propagated in suspension culture and used to generate gametes for in vitro fertilization.

2. Inducing Differentiation of Plant Stem Cells to Gametes In Vitro.

Pluripotent callus cells are differentiated in vitro to undergo meiosis and generate haploid gametes. The stem cells are cocultured in vitro with plant tissues and media which promote gametogenesis. For example, male gametes may be derived by coculture with anther-derived tissues and culture media which promote meiosis and gamete differentiation. For example, anther tissues from *Arabidopsis thaliana* including the endothecium, middle cell layer and tapetum, are cocultured with the pluripotent stem cells to initiate and support gamete formation (see e.g., Wilson et al., *Reproduction* 128: 483-492, 2004 which is incorporated herein by reference). Media and methods to promote meiosis and microspore culture may be optimized from similar described (see e.g., International Publication No. WO 03/017753 by Dirks et al., published on Mar. 6, 2003 and Wang et al., *Plant Physiol.* 124: 523-530, 2000 each of which is incorporated herein by reference). To induce female gamete differentiation in pluripotent cells tissues from the ovule, including the nucellus and integument, the tissues are cocultured with the stem cells. Methods to induce meiosis and megaspore differentiation may be optimized from similar described (see e.g., Wilson et al., Ibid. and Wang et al., 2000, Ibid.). Gametes obtained by in vitro culture and differentiation of pluripotent stem cells are "bred" by electrofusion in vitro.

3. Breeding of Haploid Gametes to Generate Hundreds of Diploid Plant Zygotes which are Sorted and Cultured In Vitro.

Gametes derived from pluripotent stem cells are "bred" by fusing pairs of gametes and culturing the diploid hybrids (i.e., zygotes) in vitro to generate cell lines and/or plant embryos. Gamete pairs are fused by applying a brief electric charge (50 msec, 1 kV/cm) to the gametes which are aligned by dielectrophoresis. Electrofusion and culture of gamete pairs in vitro may yield hundreds of plant embryos. For example, electrofusion of egg cells and sperm from maize may be done on microscope coverslips with approximately 2000 gamete pairs and yield fusion products, i.e., zygotes, which are capable of growing to become plant embryos (see e.g., Kranz et al., *The Plant Cell* 5: 739-746, 1993 which is incorporated herein by reference). Zygotes obtained by electrofusion are propagated in vitro and sorted using a fluorescence activated cell sorter (FACS). For example, multicellular structures obtained approximately 5 days after electrofusion of maize gametes are stained with fluorescent DNA stains and fluorescently labeled antibodies, and sorted into individual wells of a microtiter plate. Zygotes may be stained with propidium iodide to determine DNA content, (e.g., diploid, haploid, tetraploid, or aneuploid) and antibodies which detect cell wall components or plasma membrane components. Methods and instrumentation for flow cytometry sorting of plant cells and plant cell protoplasts are described (see e.g., Gaurav, Vishal, "Flow Cytometry of Cultured Plant Cells for Characterization of Culture Heterogeneity and Cell Sorting Applications" (2011). Open Access Dissertations. Paper 370 available online at: scholarworks.umass.edu/open_access_dissertations/370/ which is incorporated herein by reference). Zygotes with the appropriate number of chromosomes, e.g., 2n, and expressing desired cell wall or cell membrane components are cultured in vitro to generate cells for genomic selection.

4. Genomic Selection of Zygotes

Zygotes selected by cell sorting are propagated in vitro and then selected by genomic selection. Genomic selection of zygotes is done by determining the DNA sequence of single nucleotide polymorphisms (SNPs) which mark specific chromosomal loci, haplotypes and alleles. For example, SNPs may be determined by whole genome sequencing (see e.g., Resende Jr. et al., *New Phytologist* 193: 617-624, 2012 which is incorporated herein by reference). SNPs may provide markers for specific haplotypes, quantitative trait loci and individual alleles that are present in the zygotes. Next generation sequencing technology combined with other technologies is used to determine SNPs present in the individual zygote DNAs. (See e.g., Siva P. Kumpatla et al., (2012) Genomics-Assisted Plant Breeding in the 21st Century: Technological Advances and Progress, Plant Breeding, pp. 131-184, Abdurakhmonov (Ed.) InTech Publ., Rijeka, Croatia, which is included herein by reference.) For example Illumina's BeadArray platform (available from Illumina, San Diego, Calif.) uses beads with oligonucleotides attached to determine 3072 SNPs in a single reaction. Zygotes with combinations of preferred chromosomes are selected for another round of breeding and/or embryogenesis and optionally, plantlet development.

5. Cell Culture of Selected Zygotes to Obtain Stem Cells and Plantlets

Selected zygotes are cultured in vitro to obtain stem cells and/or plantlets. The zygotes resulting from electrofusion are pluripotent and give rise to flowering plants if cultured in vitro. Media and methods to propagate the zygotes in vitro may be optimized from similar described (e.g., see Kranz et al., Ibid). Alternatively to start another round of breeding the selected zygotes are differentiated in vitro to gametes (see Step 2 above) and enter another cycle of breeding, and genomic selection followed by in vitro culture to generate zygotes with improved traits. Repeated rounds of gamete cycling combined with genomic selection will reduce the time required to create highly selected plants with optimal traits.

Example 2: Rapid Breeding of Apple Trees Using Gamete Cycling In Vitro

A rapid breeding method is used to create apple trees that produce apples with desired traits in a short time frame. The rapid breeding method is used in combination with genetic marker selection to rapidly produce and select apple trees bearing multiple genetic markers that determine desired apple traits. Stem cells (apical meristem cells) are cultured in vitro and differentiated to generate gametes which are mated to produce embryos which serve as a source of stem cells for another round of breeding. Multiple embryos produced at each round of breeding are genotyped using next generation DNA sequencing technology to identify DNA markers associated with the desired apple traits.

The rapid breeding method may be initiated by in vitro fertilization using gametes from elite strains of apple trees with desired apple fruit traits. For example male gametes from a semi-sweet apple, e.g., Granny Smith, may be electrofused with egg cells from a sweet apple, e.g., Golden Delicious. Electrofusion and culture of gamete pairs in vitro may yield hundreds of plant embryos (see e.g., Kranz et al., *The Plant Cell* 5: 739-746, 1993 which is incorporated herein by reference). The resulting "Granny Smith"× "Golden Delicious" embryos are genotyped to identify embryos with a desired combination of genes from Granny Smith and Golden Delicious apple trees. For example, if a Granny Smith apple with the sweetness of a Golden Delicious apple is desired, then an embryo with a set of "sweetness genes" derived from Golden Delicious apples is selected. DNA sequencing of the apple genome has identified a set of genes associated with carbohydrate metabolism in Golden Delicious. For example, multiple copies are found of the gene encoding sorbitol-dehydrogenase which converts sorbitol to fructose in the fruit. Moreover there are 71 sorbitol metabolism and transport genes in the apple genome which may be candidates for "sweetness genes". See e.g., Velasco et al., *Nature Genetics,* 42: 833-839, 2010 which is incorporated by reference herein. Genotyping of the embryos may be done by using next generation sequencing technology to sequence specific loci, e.g., the sorbitol metabolism genes, or to survey DNA markers (e.g., single nucleotide polymorphisms (SNPs)) genome-wide. Genetic markers may be associated with desired traits in plants by whole genome sequencing or exome sequencing (see e.g., Resende Jr. et al., *New Phytologist* 193: 617-624, 2012 which is incorporated herein by reference). Genomic selection of apple tree embryos may be done approximately 10-14 days after electrofusion of gametes when a meristem part of the embryo enlarges and cells for DNA isolation and sequencing may be obtained as well as cells for induction of gametes.

Preferred embryos are selected by genomic selection and the corresponding stem cells are isolated for induction of gametes and a second round of breeding. Apple stem cells are isolated from apical meristem cells by dissection of apple embryos thus eliminating the time required for sexual maturation of trees (apple trees require approximately 10 years to mature sexually). The isolation and propagation of meristem cells are described (see e.g., U.S. Patent Appl. No. 2004/0016015 by Nguyen et al., published on Jan. 22, 2004 which is incorporated herein by reference). For example, embryo meristem cells may be obtained 8-10 days following electrofusion of gametes (see Kranz et al., Ibid.). To induce gametogenesis in plant stem cells, in vitro cultures are established in conjunction with gene expression vectors encoding transcription factors essential to gametogenesis. Methods to induce gamete production from embryonic stem cells in mice are described (see e.g., Hayashi et al., *Science* 338: 971-975, 2012 and Nayemia et al., *Developmental Cell* 11: 125-132, 2006 which are incorporated herein by reference). To generate apple male gametes, an in vitro culture system for apple apical meristem cells is established with plant hormones and nutrients. Methods to culture meristem cells in vitro are known (see e.g., U.S. Patent Appl. No. 2004/0016015, Ibid.). To promote differentiation of the stem cells to gametes, vectors encoding transcription factors essential for male gamete production are transfected into the stem cells. For example, MADS-box genes encoding essential transcription factors include: SPOROCYTELESS (SPL)/NOZZLE (NZZ), AGAMOUS-LIKE 66 (AGL66) and AGL104 (see e.g., Gramzow et al., *Genome Biology* 11: 214, 2010 available online at: http://genomebiology.com/ 2010/11/6/214 which is included herein by reference). Plasmid expression vectors containing MADS-box genes may be derived from *Agrobacterium tumefaciens* Ti plasmids (see e.g., U.S. Pat. No. 7,612,258 issued to He et al. on Nov. 3, 2009 which is incorporated herein by reference). Expression vectors with promoter sequences, MADS-box genes, selectable markers (e.g. Hygromycin resistance gene) and regulatory sequences may be transferred into stem cells by microprojectile bombardment or electroporation (see e.g., U.S. Patent Appl. 2004/0016015, Ibid.) Similarily a vector encoding AGL23, may be used to promote female gamete (i.e., egg cell) differentiation in apple stem cells. MADS-box genes essential to gametogenesis are described (see e.g., Gramzow et al., Ibid.)

Gametes derived from the meristem cells of genetically selected apple tree embryos are bred again to improve the apple tree genotype. For example, zygotes bearing "sweetness genes", e.g., the Golden Delicious alleles for sorbitol metabolism and transport may be crossed with Golden Delicious gametes to capture both alleles at each "sweetness gene" locus. Domesticated apple trees such as Golden Delicious are highly heterozygous, and in addition multiple genes may be required to control a single trait such as sweetness (see e.g., Velasco et al., Ibid.). A second round of electrofusion generates hundreds of zygotes which are cultured in vitro for 10-14 days and then genetically selected by DNA sequencing of sorbitol metabolism and transport genes or associated SNP's (as described above). Progeny are selected that contain Golden Delicious alleles at the sorbitol gene loci and Granny Smith alleles at other loci. Meristem cells may be isolated and induced to generate male and female gametes for another round of breeding.

Repeated breeding cycles coupled with genetic selection using next generation sequencing technology allows rapid development of apple trees with traits such as sweetness which are controlled by multiple heterozygous genes. For example, apple tree embryos with multiple sorbitol metabolism genes derived from Golden Delicious on a background of Granny Smith genes may be selected in multiple crosses which require approximately 11-15 days each. In vitro culture and plant outgrowth of multiple preferred apple tree embryos may be done by optimizing similarly described

Example 3: Rapid Breeding of Cotton by In Vitro Gamete Cycling

To develop improved cotton cultivars a rapid breeding method is employed that induces stem cells to differentiate directly to gametes which are mated and propagated in vitro. An elite cotton cultivar is crossed with a second elite cultivar to select for a desired trait, for example, drought resistance. Rapid breeding is combined with genomic selection to identify preferred progeny emanating from an initial cross and multiple backcrosses.

The rapid breeding method may be initiated by in vitro fertilization using gametes from elite cotton cultivars, e.g., *Gossypium hirsutum*, cv. Siv'on (GH) and *Gossypium barbadense*, cv. F-177 (GB) which carry quantitative trait loci (QTL) conferring drought resistance (see e.g., Levi et al. *Mol. Breeding* 23: 179-195, 2009 which is incorporated herein by reference). For example male gametes from GH may be electrofused with gametes from GB. Electrofusion and culture of gamete pairs in vitro may yield hundreds of plant embryos (see e.g., Kranz et al., *The Plant Cell* 5: 739-746, 1993 which is incorporated herein by reference). The resulting "GH×GB" embryos are genotyped to identify embryos bearing chromosomal loci conferring draught resistance: For example QTL on chromosome 6 and chromosome 2 of GB are associated with drought resistance, and QTL on chromosome 25 and chromosome 22 of GH were also linked to drought resistance (see Levi et al., Ibid.). Genotyping of the embryos may be done by using next generation sequencing technology to sequence specific loci, e.g., QTL, or to survey DNA markers (e.g., single nucleotide polymorphisms (SNPs)) genome-wide. For example SNPs identifying GH chromosomes versus GB chromosomes may be used for genomic selection (see e.g., Yu et al., *G3, Genes; Genomes; Genetics* 2: 43-58, 2012 and Resende Jr. et al., *New Phytologist* 193: 617-624, 2012 which are incorporated herein by reference). Genotyping of cotton embryos is done using next generation sequencing technology. For example the Illumina Infinium assay (available from Illumina, San Diego, Calif.) is used to determine cotton SNPs using software also available from Illumina. Genomic selection of cotton embryos may be done approximately 10-14 days after electrofusion of gametes when a meristem part of the embryo enlarges and cells for DNA isolation and sequencing may be obtained as well as cells for induction of gametes (see Kranz et al., Ibid.). Alternatively polymerase chain reaction (PCR) and agarose gels may be used to identify embryos containing a specific gene (see e.g., Wang et al., *Plant Breeding* 130: 569-573, 2011 which is incorporated herein by reference).

Cotton embryo hybrids bearing GH chromosomes conferring drought resistance are backcrossed to the elite cotton cultivar, GB, to restore the GB genetic background. Gamete cycling and genomic selection are used to expedite the breeding process and eliminate the time needed for sexual maturation of the cotton embryos. For example the generation time for cotton plants in the field is approximately 130-140 days (e.g., see Wang et al., 2011, Ibid.) versus a generation time of approximately 11-15 days using gamete cycling in vitro.

Hybrid embryos (GH×GB) bearing the drought-resistance loci are dissected to obtain pluripotent meristem cells which are cultured in vitro to induce gamete formation. Meristem cells that are pluripotent stem cells are isolated from the hybrid embryos, where they appear 8-10 days after electrofusion of gametes (see e.g., Kranz et al., Ibid.). The stem cells are cocultured in vitro with plant tissues and media which promote gametogenesis. For example, male gametes may be derived by coculture with anther-derived tissues and culture media which promote meiosis and gamete differentiation. For example, anther tissues from GH including the endothecium, middle cell layer and tapetum are cocultured with the hybrid stem cells to support gamete formation (see e.g., Wilson et al., *Reproduction* 128: 483-492, 2004 which is incorporated herein by reference). Media and methods to promote meiosis and microspore culture have been described (see e.g., International Publication No. WO 03/017753 by Dirks et al., published on Mar. 6, 2003 and Wang et al., *Plant Physiol.* 124: 523-530, 2000 which are incorporated herein by reference). For example media for cotton anther and ovule culture in vitro are described (see e.g., Memon et al., *World Applied Sciences Journal* 8: 76-79, 2010 which is incorporated herein by reference). Murashige and Skoog media with 2,4 dichlorophenoxyacetic acid (2,4-D), indole-3-acetic acid (IAA), indole-3-butyric acid (IBA), and kinetin (6-furfuryl-aminopurine) (all available from Sigma-Aldrich Corp., St. Louis, Mo.) may be used to culture ovule and anther tissues. The plant hormone abscisic acid may be added to promote androgenesis (see e.g., Wang et al., 2000, Ibid.). Gametes derived from the stem cells of genetically selected embryos are bred again to improve the cotton cultivar. For example the preferred hybrid embryos (GH×GB) may be backcrossed with GB to create an improved drought-resistant strain with all the positive traits of GB.

Gametes derived from genomically selected GH×GB embryo's meristem cells are bred with GB gametes to obtain cotton with predominantly GB genes and multiple GH genes conferring drought-resistance. Multiple chromosomal loci may be required to confer a single trait such as drought resistance (see e.g., Levi et al., Ibid.). A second round of electrofusion generates hundreds of zygotes which are cultured in vitro for 10-14 days and then genetically selected by DNA sequencing of specific loci or the corresponding SNP's (as described above). Progeny are selected that retain GH drought-resistance loci and carry predominately GB chromosomes otherwise. The selected embryos may be used as a source of stem cells and gametes for another round of breeding. For example, a breeding program may include four backcross generations to select an optimal cultivar with an improved trait. The rapid cycling of gametes method requires approximately 60 days to complete four backcrosses versus approximately 360 days for four generations using alternative methods (see e.g., Wang et al., 2011, Ibid.).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   one or more input/output devices having a non-transitory signal bearing medium operable to
   select one or more plant stem cells;
   execute a first protocol for induction of at least one of the plant stem cells to differentiate into at least one first gamete;
   execute a second protocol for combining the at least one first gamete and at least one second gamete for fertilization; and receive at least one input information relating to one or more desired genotype characteristics of the progeny plant or progeny plant cells resulting from the fertilization;

compare the at least one input information relating to the one or more desired genotype characteristics of the progeny plant or progeny plant cells with a Desired Characteristic Value dataset;

generate a Desired Characteristic Value based on the comparison;

reinitiate receiving at least one input information relating to one or more desired genotype characteristics of the progeny plant or progeny plant cells, at least one input with the Desired Characteristic Value dataset, generating a Desired Characteristic Value based on the comparison until an assessment threshold is satisfied; and when the threshold is satisfied, executing a third protocol for induction of at least one of the plant stem cells to differentiate into at least one progeny cell-generated second round gamete.

2. The system of claim 1, further including receiving at least one third input information relating to one or more desired characteristics of a second generation of progeny plant or progeny plant cells resulting from a second round of fertilization of at least one first generation progeny plant or progeny plant cell.

3. The system of claim 1, wherein the progeny plants or progeny plant cells include multiple plants or plant cells from the same round of fertilization.

4. The system of claim 1, wherein the assessment threshold includes a predetermined threshold.

5. The system of claim 1, wherein the assessment threshold includes one or more of a period of time, characteristic value, progeny location, or disease or death of the progeny.

6. The system of claim 1, wherein the Desired Characteristic Value includes a quantitative evaluation of at least one desired phenotypic characteristic.

7. The system of claim 6, wherein the at least one desired phenotypic characteristic includes at least one of increased yield, improved nutritional content, increased growth or development, or increased stress resistance or tolerance.

8. The system of claim 7, wherein the increased nutritional content includes increased seed oil or protein content, or increased nutrition in any edible portion of the plant.

9. The system of claim 7, wherein increased stress resistance or tolerance includes increases resistance to drought, pathogens, disease, temperature, light, osmotic stress, or low nutrient environment.

10. The system of claim 7, wherein the increased yield includes at least one of increased plant height, improved plant structure, increased assimilation of nutrients, increased pod number or better position on the plant, improved pod shatter, increased grain size, increased efficiency of nitrogen fixation, better seedling vigor, increased percentage of seed germination, increased growth rate, increased seed number or size, or increased size composition.

11. The system of claim 1, wherein the Desired Characteristic Value includes a quantitative evaluation of at least one desired epigenetic characteristic.

12. The system of claim 1, wherein the input information includes at least one of information obtained directly from a sensor, or information observed by a worker.

13. The system of claim 1, wherein the input information includes at least one detected phenotypic characteristic sensed by one or more sensors assessing the progeny.

14. The system of claim 1, wherein the input information includes at least one of a detected phenotypic characteristic entered by a worker.

15. The system of claim 14, wherein the worker includes at least one of a farm implement, an unmanned aerial vehicle, or a person.

16. The system of claim 1, wherein the one or more input/output devices is operable to convert information into electronic signals that include digitized or weighted protocols.

17. The system of claim 1, wherein the Desired Characteristic Value includes a quantitative evaluation of at least one desired genetic characteristic.

* * * * *